United States Patent [19]
Dodey et al.

[11] Patent Number: 6,063,791
[45] Date of Patent: May 16, 2000

[54] N-BENZENESULFONYL-L-PROLINE DERIVATIVES, METHOD FOR PREPARING AND THERAPEUTIC USE

[75] Inventors: Pierre Dodey, Fontaine-lés-Dijon; Michel Bondoux, Fontaine-les-Dijon; Patrick Houziaux, Bazemont; Martine Barth, Dijon; Khan Ou, Hauteville-lès-Dijon, all of France

[73] Assignee: Fournier Industrie et Sante, Paris, France

[21] Appl. No.: 09/297,845

[22] PCT Filed: Nov. 14, 1997

[86] PCT No.: PCT/FR97/02049

§ 371 Date: May 6, 1999

§ 102(e) Date: May 6, 1999

[87] PCT Pub. No.: WO98/24783

PCT Pub. Date: Jun. 11, 1998

[30] Foreign Application Priority Data

Dec. 4, 1996 [FR] France .................................. 96 14891

[51] Int. Cl.[7] .......................... C07D 215/16; A61K 31/47
[52] U.S. Cl. ........................... 514/314; 546/177; 546/178
[58] Field of Search .................................. 546/177, 178; 514/314

[56] References Cited

FOREIGN PATENT DOCUMENTS

| | | |
|---|---|---|
| 0 261 539 B1 | 3/1988 | European Pat. Off. |
| 0 622 361 A1 | 2/1994 | European Pat. Off. |
| 0 596 406 B1 | 5/1994 | European Pat. Off. |
| 36 17 183 A1 | 5/1987 | Germany. |

OTHER PUBLICATIONS

K.D. Bhoola et al., "Bioregulation of Kinins: Kallikreins, Kininogens, and Kininases," *Pharmacological Reviews*, vol. 44, No. 1, 1992, pp. 1–80.

John M. Stewart, "Bradykinin Antagonists: Development and Applications," *Biopolymers (Peptide Science)*, vol. 37, 1995, pp. 143–155.

*Primary Examiner*—D. Margaret Seaman
*Attorney, Agent, or Firm*—Evenson, McKeown, Edwards & Lenahan, PLLC

[57] ABSTRACT

The present invention relates to compounds selected from the group consisting of
(i) the compounds of formula I:

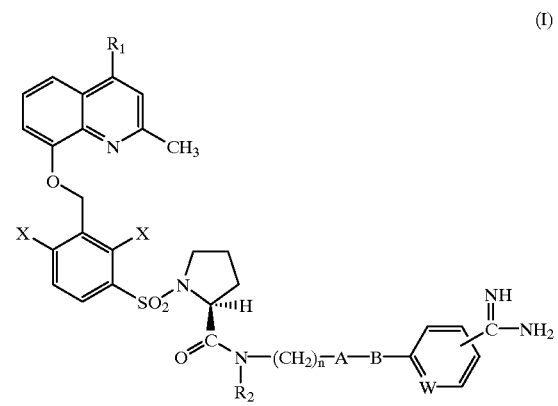

in which:
X is a halogen atom or a methyl group,
A is a group —N($R_3$)CO— or —CO—N($R_3$)—,
B is a single bond, —$CH_2$— or —$CH_2$—O—,
$R_1$ is H, a $C_1$–$C_3$ alkyl group or a $CF_3$ group,
$R_2$ and $R_3$ are each independently H or a $C_1$–$C_3$ alkyl group,
W is CH or N, and
n is 2, 3, 4 or 5; and
(ii) their addition salts.
It further relates to the process for their preparation and to their use in therapeutics, especially for combating pathological conditions involving bradykinin.

12 Claims, No Drawings

N-BENZENESULFONYL-L-PROLINE DERIVATIVES, METHOD FOR PREPARING AND THERAPEUTIC USE

FIELD OF THE INVENTION

The present invention relates to novel compounds derived from N-(benzenesulfonyl)-(L)-proline, to the process for their preparation and to their use in therapeutics.

These novel compounds have an antagonistic action towards bradykinin and are useful in therapeutics, particularly for the treatment of pain and inflammation and especially for the treatment of asthma, cerebral traumatic shock and allergic rhinitis.

PRIOR ART

It is known that one of the possible treatments for certain pathological conditions of a painful and/or inflammatory nature (such as asthma, rhinitis, septic shock, toothache, etc.) is to inhibit the action of certain hormones such as bradykinin or kallidin. These peptide hormones are in fact involved in a large number of physiological processes, some of which are closely associated with these pathological conditions.

Although no product possessing this mode of action has yet been marketed, numerous studies have been undertaken in order to understand the mode of action of kinins, particularly bradykinin and its homologs, and then to create compounds capable of antagonizing the bradykinin receptors. Pharmacological Reviews vol. 44 no. 1, pages 1–80 (1992) and Biopolymers (Peptide Science) vol. 37, pages 143–155 (1995) may be cited among the numerous publications reporting this work.

Bradykinin is a peptide hormone consisting of 9 amino acids (Arg-Pro-Pro-Gly-Phe-Ser-Pro-Phe-Arg) and kallidin is a peptide hormone (Lys-Arg-Pro-Pro-Gly-Phe-Ser-Pro-Phe-Arg) which contains an additional amino acid (Lys) compared with bradykinin. It is known that earlier studies made it possible to obtain peptides which interact with the bradykinin receptors: some of them, like bradycor (CP.0127 from CORTECH), icatibant (HOE 140 from HOECHST) ["bradycor" and "icatibant" are international non-proprietary names (INN)] or NPC 17761 (from SCIOS-NOVA), have an inhibitory action on the binding of bradykinin to its $B_2$ receptor. More recently, non-peptide compounds have been proposed as antagonists towards the binding of bradykinin to its $B_2$ receptor, especially in EP-A-0596406 and EP-A-0622361. It is also known that certain compounds which are structurally related to the compounds referred to in the two patent applications cited above have already been described for their possible anti-thrombotic properties, especially in the publications DE-A-3617183 and EP-A-0261539.

OBJECT OF THE INVENTION

There is a need for reducing or eliminating pain and inflammation in mammals and particularly in man.

To meet this need, a novel technical solution has been sought which is effective in the treatment of pain, irrespective of its origin, and especially in the treatment of (i) pain associated with inflammatory phenomena, and (ii) inflammation.

According to the invention, it is proposed to provide a novel technical solution which involves competitive binding, at the bradykinin $B_2$ receptor, between (i) bradykinin and related or analogous hormones, and (ii) an antagonist, and utilizes compounds of the benzenesulfonamide type which are structurally different from the known products mentioned above and which are capable of limiting or substantially inhibiting the binding of bradykinin and analogous hormones to said bradykinin $B_2$ receptor.

According to this technical solution, the novel compounds bind competitively to the bradykinin $B_2$ receptor without causing the effects of bradykinin on this receptor (the substance is said to be an antagonist). This results in the appearance of a state analogous to that observed in the absence of bradykinin, namely a reduction in pain and inflammatory reactions.

According to this novel technical solution, it is proposed according to a first aspect of the invention to provide compounds derived from N-(benzenesulfonyl)-(L)-proline as novel industrial products, according to a second aspect of the invention to provide a process for the preparation of these compounds, and according to a third aspect of the invention to provide the use of these compounds, especially in therapeutics, as analgesics and/or anti-inflammatories.

SUBJECT OF THE INVENTION

According to the novel technical solution of the invention, an N-(benzenesulfonyl)-L-proline compound is recommended as a novel industrial product, said compound being selected from the group consisting of:

(i) the compounds of formula I:

in which:

X is a halogen atom or a methyl group,
A is a group —N(R$_3$)—CO— or —CO—N(R$_3$)—,
B is a single bond, —CH$_2$— or —CH$_2$—O—,
R$_1$ is a hydrogen atom, a C$_1$–C$_3$ alkyl group with a linear or branched hydrocarbon chain, or a trifluoromethyl group,
R$_2$ and R$_3$ are each independently a hydrogen atom or a C$_1$–C$_3$ alkyl group with a linear or branched hydrocarbon chain,
W is CH (in which case the aromatic ring is a phenyl group) or N (in which case the aromatic ring is a pyridinyl group), and
n is 2, 3, 4 or 5; and (ii) their addition salts.

According to the invention, a process for the preparation of the compounds of formula I and their addition salts is also recommended.

The use of an antagonist of a receptor of bradykinin and hormones analogous to bradykinin is also recommended, wherein a bradykinin $B_2$ receptor antagonist selected from the compounds of formula I and their non-toxic addition salts is used to obtain a drug intended for use in therapeutics to combat pathological conditions involving bradykinin or its analogs, in particular to combat pain, and especially in the treatment or prevention of pathological conditions associated with inflammatory or painfull states.

DETAILED DESCRIPTION OF THE INVENTION

In general formula I of the compounds of the invention, halogen atom is understood as meaning a fluorine, chlorine, bromine or iodine atom, the preferred halogen being the chlorine atom.

$C_1$–$C_3$ alkyl group with a linear or branched hydrocarbon chain is understood here as meaning the methyl, ethyl, propyl or 1-methylethyl group.

In the compound of formula I, the nitrogen heterocycle of the pyrrolidine type comprises 1 asymmetric carbon atom. According to the invention, this carbon has the S configuration, which corresponds to the configuration of L-proline.

As indicated in the general formula of the compounds according to the invention, the structure comprises an amidine group, —C(=NH)NH$_2$, on an aromatic ring; this amidine group can occupy any substitutable position on its aromatic ring; in particular, it can be located in the 2-, 3- or 4-position if said ring is phenyl, or in the 3-, 4-, 5- or 6-position if said ring is pyridinyl.

"Addition salts" are understood as meaning the acid addition salts obtained by reacting a compound of formula I with a mineral acid or an organic acid. The preferred mineral acids for salifying a basic compound of formula I are hydrochloric, hydrobromic, phosphoric and sulfuric acids. The preferred organic acids for salifying a basic compound of formula I are methanesulfonic, benzenesulfonic, maleic, fumaric, oxalic, citric, lactic and trifluoroacetic acids.

The general process recommended according to the invention for the preparation of the compounds of formula I comprises the steps which consist in:

(1) reacting an acid of formula II:

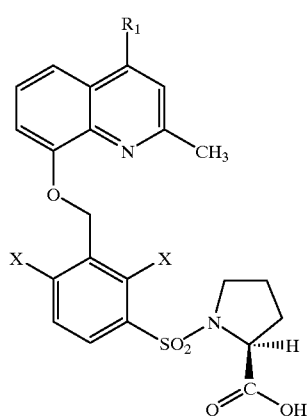

(II)

in which:

$R_1$ is a hydrogen atom, a $C_1$–$C_3$ alkyl group with a linear or branched hydrocarbon chain, or a trifluoromethyl group, and X is a halogen or a methyl group, with an amine of formula III:

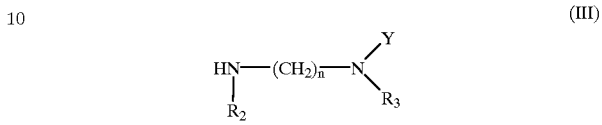

(III)

in which:

$R_2$ and $R_3$ are each independently a hydrogen atom or a $C_1$–$C_3$ alkyl group, n is 2, 3, 4 or 5, and Y is an amino-protecting group, for example the group Boc (1,1-dimethylethoxycarbonyl), in a solvent, for example dichloromethane or dimethylformamide, in the presence of at least one activator commonly used to create linkages of the peptide types, for example (1-(3-dimethylaminopropyl)-3-ethylcarbodiimide hydrochloride (EDCI) and 1-hydroxy-7-azabenzotriazole (HOAT), at a temperature near room temperature (i.e. a temperature of between about 0 and about 40° C. and preferably a temperature of between 10 and 35° C.), for 2 to 50 hours, to give a compound of formula (IV):

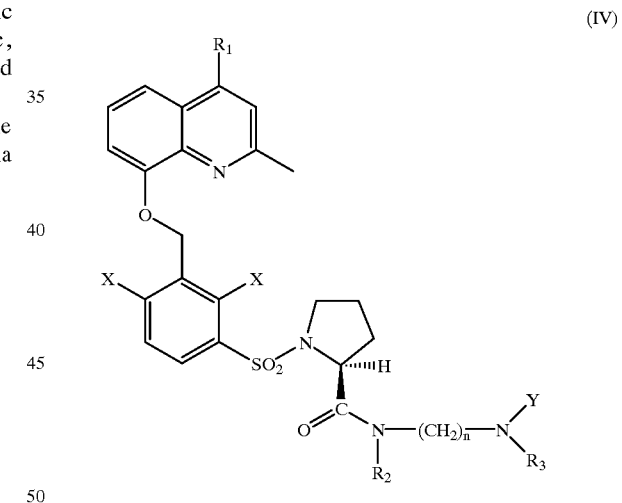

(IV)

in which $R_1$, $R_2$, $R_3$, X, Y and n are as defined above;

(2) deprotecting the resulting compound of formula IV so as to replace the protecting group Y with a hydrogen atom, for example, if Y is the group Boc, by reacting the compound of formula IV with trifluoroacetic acid in a solvent such as dichloromethane or ethyl acetate, at room temperature (15–25° C.), for 5 to 30 hours, to give the compound of formula V:

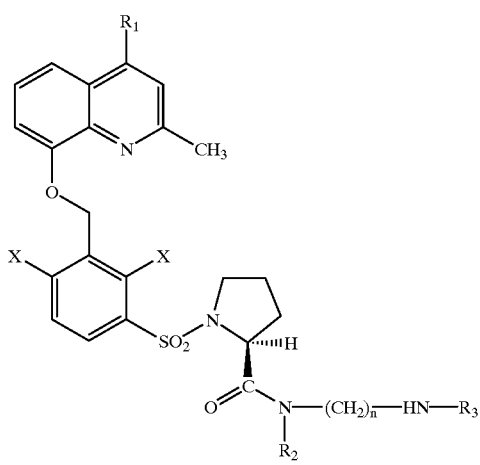

(V)

in which $R_1$, $R_2$, $R_3$, X and n are as defined above; (as a variant of this process, the group Boc can be replaced by reaction with aqueous hydrochloric acid solution, the compound of formula IV being allowed to react for 1 to 10 hours at a temperature of between 30 and 60° C., in which case the compound of formula V is obtained in the form of the dihydrochloride); and (3) reacting the resulting compound of formula V with an acid of formula VI:

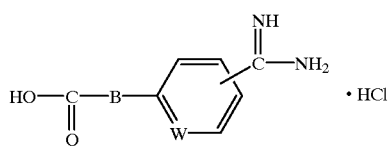

(VI)

in which:

B is a single bond or a group —$CH_2$— or —$CH_2$—O—, and

W is —CH— or N, under conditions analogous to those recommended for step (1) above, and, if necessary, in the presence of a base such as N-methylmorpholine if the amine of formula V is reacted in its salified form, to give the compound of formula I:

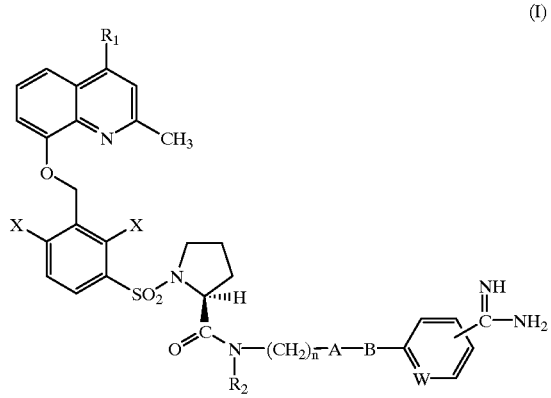

(I)

in which:

A is —N($R_3$)—CO—,
B is a single bond, —$CH_2$— or —$CH_2$—O—, $R_1$ is a hydrogen atom, a $C_1$–$C_3$ alkyl group or a trifluoromethyl group, $R_2$ and $R_3$ are each independently H or a $C_1$–$C_3$ alkyl group, X is a halogen or a methyl group, W is CH or N, and n is 2, 3, 4 or 5.

In a first variant, A, the compound of formula I (in which A is —N($R_3$)—CO—) can be obtained by reacting a compound of formula V, obtained according to step (2) above, with an acid chloride of formula VII:

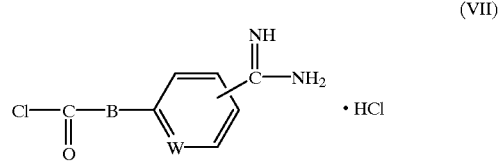

(VII)

in which:

B is a single bond, —$CH_2$— or —$CH_2$—O—, and

W is CH or N, in a solvent, for example dichloromethane, and in the presence of an aprotic base, for example N-methylmorpholine, at a temperature near room temperature, for 2 to 30 hours.

In a second variant, called B, (a) the compound of formula V, obtained in step (2) above, is reacted with a compound of formula VIII:

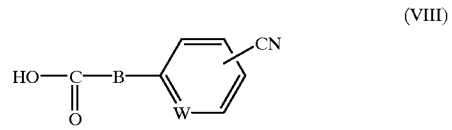

(VIII)

in which:

B is a single bond, —$CH_2$— or —$CH_2$O—, and

W is CH or N, under operating conditions analogous to those of step (3) described above, to give a compound of formula IX:

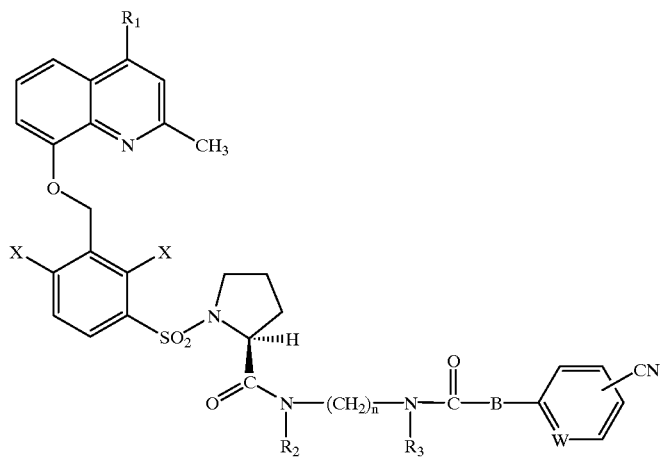

(IX)

in which $R_1$, $R_2$, $R_3$, X, W, n and B are as defined in the starting materials; (b) the resulting compound of formula IX is reacted with hydroxylamine (freed from its hydrochloride in the reaction medium by reaction with a base such as triethylamine), in a solvent, for example dimethyl sulfoxide (DMSO), at room temperature, for 2 to 12 hours, to give the compound of formula X:

in which $R_1$, $R_2$, $R_3$, X, W, n and B are as defined above; (c) the resulting compound of formula X is reacted with excess acetic anhydride in a solvent, for example dichloromethane, at room temperature, for 1 to 15 hours, to give the compound of formula XI:

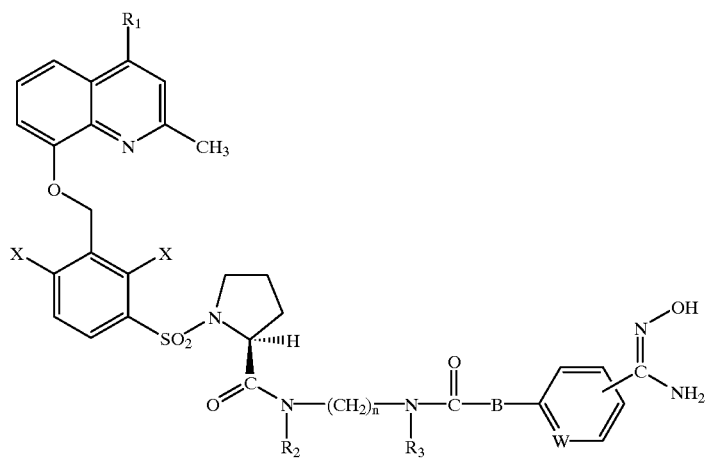

(X)

(XI)

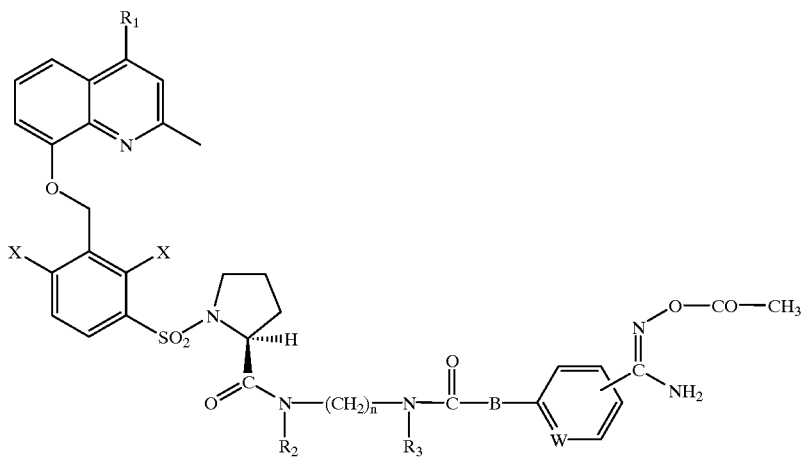

in which $R_1$, $R_2$, $R_3$, X, W, n and B are as defined above; and (d) the resulting compound of formula XI is catalytically hydrogenated in a solvent, for example methanol, in the presence of a hydrogenation catalyst such as Lindlar's catalyst, at room temperature, under a hydrogen pressure of between $10^5$ and $5.10^5$ Pa, to give the compound of formula I in which $R_1$, $R_2$, $R_3$, X, W, n and B are as defined above, A is the group —N($R_3$)—CO— and the amidine group retains the initial position of the cyano group of the starting acid.

In a third variant, called C, of the process for the preparation of a compound according to the invention, it is recommended to (α) react an acid of formula II:

(II)

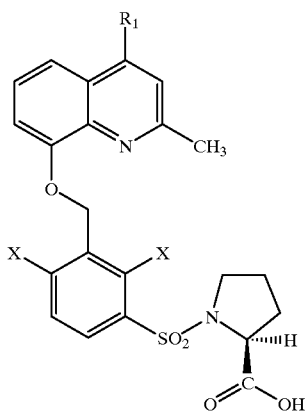

in which:

$R_1$ is a hydrogen atom, a $C_1$–$C_3$ alkyl group with a linear or branched hydrocarbon chain, or the trifluoromethyl group, and X is a halogen or the methyl group, with an amine of formula XII:

(XII)

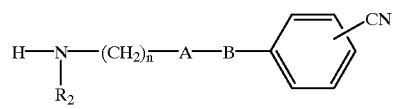

in which:

A is a group —N($R_3$)—CO— or a group —CO—N($R_3$)—,

B is a single bond, —$CH_2$— or —$CH_2$—O—, $R_2$ and $R_3$ are each independently H or a $C_1$–$C_3$ alkyl group, n is 2, 3, 4 or 5, and W is CH or a nitrogen atom, under conditions analogous to those described above in step (1) of the general process, to give a compound of formula IXa:

(IXa)

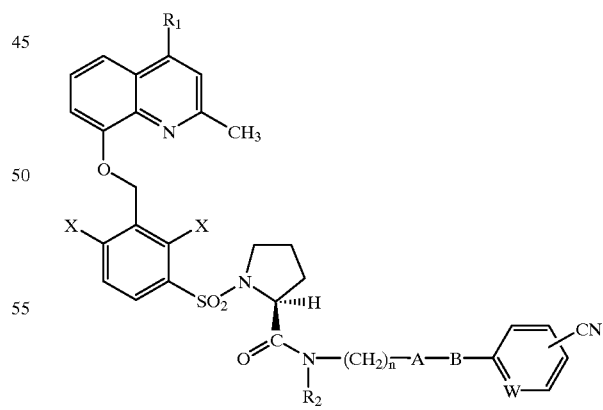

in which A, B, $R_1$, $R_2$, $R_3$, X, W and n are as defined in the starting materials; and (β) carry out the steps analogous to those described above in variant B to give the compound of formula I from the compound of formula IXa by conversion of the cyano group to an amidine group.

If necessary, the compound of formula I, normally obtained in the form of the free base according to the above procedures, can be converted to one of its salts with an acid by reaction with said acid, generally in excess and in solution in a solvent.

The invention will be understood more clearly from the following Preparatory Examples and the results of pharmacological tests obtained with compounds according to the invention.

Of course, these details as a whole do not imply a limitation but are given by way of illustration.

In the case of compounds which have an asymmetric carbon in their structure, the absence of a particular indication, or the notation (R,S), means that the compounds are racemic; in the case of compounds which exhibit chirality, this is indicated immediately after the numbering of the substituent carried by said asymmetric carbon; the symbol (R) or (S) is then used in accordance with the Cahn-Ingold-Prelog rules. The nomenclature used in the Examples is that recommended by Chemical Abstracts; thus, after reaction of the acid group with an amine, certain L-proline derivatives may become 2(S)-pyrrolidinecarboxamide derivatives.

In the experimental section, the "Preparations" relate to the intermediates and the "Examples" relate to the products according to the invention.

The melting points (m.p.) indicated below are generally measured using a Koffler bench and are not corrected, so they represent instantaneous melting points.

The spectral characteristics of the nuclear magnetic resonance (NMR) signals are given for the proton ($^1$H) or for the 13 isotope of carbon ($^{13}$C); the chemical shift is indicated relative to the tetramethylsilane signal and is followed, in brackets, by the shape of the signal (s for singlet, d for doublet, t for triplet, q for quadruplet, m for multiplet, bs for broad signal) and the number of protons corresponding to the signal. By way of indication, the $^1$H NMR spectra were run at 300 MHz.

EXAMPLE 1

1-[[3-[(2,4-Dimethylquinolin-8-yl)oxymethyl]-2,4-dichlorophenyl]sulfonyl]-N-[2-[[4-(aminoiminomethyl)phenyl]carbonylaminol]ethyl]-2(S)-pyrrolidinecarboxamide A solution of 0.15 g ($7.25.10^{-4}$ mol) of 4-(aminoiminomethyl)benzoic acid hydrochloride in 10 ml of dimethylformamide (DMF) is prepared and 0.15 g ($7.98.10^{-4}$ mol) of 1-(3-dimethylaminopropyl)-3-ethylcarbodiimide hydrochloride (EDCI) and 0.11 g ($7.25.10^{-4}$ mol) of 1-hydroxy-7-azabenzotriazole (HOAT) are added. The resulting mixture is stirred for 30 minutes at room temperature (about 20° C.) and a solution of 0.4 g ($7.25.10^{-4}$ mol) of 1-[[3-[(2,4-dimethylquinolin-8-yl)oxymethyl]-2,4-dichlorophenyl]sulfonyl]-N-[2-aminoethyl]-2(S)-pyrrolidine-carboxamide in 10 ml of DMF is then added dropwise. The reaction medium is stirred for 5 hours at room temperature and then poured into iced water. 1 N sodium hydroxide solution is then added slowly until the pH is 8, after which the mixture is extracted with dichloromethane. The organic phase is washed with water, dried over sodium sulfate and then concentrated under reduced pressure. The crude product is purified by chromatography on NH$_2$-grafted silica gel (LICHROPREP® NH$_2$) using a dichloromethane/methanol mixture (95/5; v/v) as the eluent to give 0.2 g of the expected product (yield=40%). The product is used directly to obtain the salt.

EXAMPLE 2

1-[[3-[(2,4-Dimethylquinolin-8-yl)oxymethyl]-2,4-dichlorophenyl]sulfonyl]-N-[2-[[4-(aminoiminomethyl)phenyl]carbonylamino]ethyl]-2(S)-pyrrolidine-carboxamide dihydrochloride 0.2 g ($0.287.10^{-3}$ mol) of the compound obtained according to Example 1 is dissolved in 2 ml of 1 N hydrochloric acid solution. The solution obtained is lyophilized. The lyophilization residue is redissolved in 2 ml of distilled water and lyophilized again to give 220 mg of the expected compound in the form of an amorphous white solid (quantitative yield). M.p.=198° C. $[\alpha]_D^{27}$=−38° (c=0.31; CH$_3$OH)

EXAMPLE 3

1-[[3-[(2,4-Dimethylquinolin-8yl)oxymethyl]-2,4-dichlorophenyl]sulfonyl]-N-[2-[[2-[4-(aminoiminomethyl)phenoxy]-1-oxoethyl]amino]ethyl]-2(S)-pyrrolidinecarboxamide The expected product is obtained in the form of a white solid (yield=31%) by following a procedure analogous to Example 1, starting from 4-(aminoiminomethyl)phenoxyacetic acid hydrochloride. M.p.=156–160° C. $[\alpha]_D^{23}$=−30° (c=0.25; CH$_3$OH)

EXAMPLE 4

1-[[3-[(2,4-Dimethylquinolin-8-yl)oxymethyl]-2,4-dichlorophenyl]sulfonyl]-N-[2-[[2-[4-(aminoiminomethyl)phenoxy]-1-oxoethyl]amino]ethyl]-2(S)-pyrrolidinecarboxamide dihydrochloride The expected product (practically quantitative yield) is obtained by following a procedure analogous to Example 2, starting from the compound obtained according to Example 3. M.p.=184–188° C. $[\alpha]_D^{24}$=−27° (c.=0.3; CH$_3$OH)

EXAMPLE 5

1-[[3-[(2,4-Dimethylquinolin-8-yl)oxymethyl]-2,4-dichlorophenyl]sulfonyl]-N-[3-[[4-(aminoiminomethyl)phenyl]carbonylamino]propyl]-2(S)-pyrrolidine-carboxamide The expected product (yield=48%) is obtained by following a procedure analogous to Example 1, starting from 1-[[3-[(2,4-dimethylquinolin-8-yl)oxymethyl]-2,4-dichlorophenyl]sulfonyl]-N-[3-aminopropyl]-2(S)-pyrrolidinecarboxamide hydrochloride and in the presence of N-methylmorpholine. M.p.=178–180° C. $[\alpha]_D^{25}$=−39° (c=0.32; CH$_3$OH)

EXAMPLE 6

1-[[3-[(2,4-Dimethylquinolin-8-yl)oxymethyl]-2,4-dichlorophenyl]sulfonyl]-N-[3-[[4-(aminoiminomethyl)phenyl]carbonylamino]propyl]-2(S)-pyrrolidine-carboxamide dihydrochloride A solution of 1.3 g ($1.82.10^{-3}$ mol) of the compound obtained according to Example 5 in 20 ml of ethyl acetate and 6 ml of ethanol is prepared. 1.4 ml of a saturated solution of hydrogen chloride in ethyl ether are added. The crystals formed are filtered off, washed with ethyl ether and then redissolved in 25 ml of distilled water. The solution obtained is lyophilized to give 1.25 g of the expected product in the form of an amorphous white solid (yield=87.4%). M.p=200–202° C. $[\alpha]_D^{25}$=−36° (c=0.3; CH$_3$OH)

EXAMPLE 7

1-[[3-[(2,4-Dimethylquinolin-8-yl)oxymethyl]-2,4-dichlorophenyl]sulfonyl]-N-[3-[[2-[4-(aminoiminomethyl)phenyl]-1-oxoethyl]amino]propyl]-2(S)-pyrrolidinecarboxamide The expected product (yield=39%) is obtained by following a procedure analogous to Example 5, starting from 4-(aminoiminomethyl)phenylacetic acid hydrochloride. M.p.=184–188° C. $[\alpha]_D^{24}$=−30° (c=0.3; $CH_3OH$)

Example 8

1-[[3-[(2,4-Dimethylquinolin-8-yl)oxymethyl]-2,4-dichlorophenyl]sulfonyl]-N-[-[[2-[4 (aminoiminomethyl)phenyl]-1-oxoethyl]amino] propyl]-2(S)-pyrrolidinecarboxamide dihydrochloride A solution of 120 mg (0.165.10$^{-3}$ mol) of the compound obtained according to Example 7 in 5 ml of ethanol is prepared and 1 ml of a saturated solution of hydrogen chloride in ethyl ether is added. After the mixture has been stirred for 30 minutes at room temperature, the reaction medium is concentrated under reduced pressure. The residue is redissolved in 10 ml of water. After filtration, the solution is lyophilized to give 130 mg of the expected product in the form of a white solid (yield=98%). M.p.=186–190° C. $[\alpha]_D^{24}$==25° (c=0.30; $CH_3OH$)

EXAMPLE 9

1-[[3-[(2,4-Dimethylquinolin-8-yl)oxymethyl]-2,4-dichlorophenyl]sulfonyl]-N-[3-[[2-[4 (aminoiminomethyl)phenoxy]-1-oxoethyl]amino] propyl]-2(S)-pyrrolidinecarboxamide The expected product (yield=35%) is obtained by following a procedure analogous to Example 7, starting from 4-(aminoiminomethyl)phenoxyacetic acid hydrochloride. M.p.=124–128° C. $[\alpha]_D^{24}$=−21° (c=0.32; $CHCl_3$)

EXAMPLE 10

1-[[3-[(2,4-Dimethylquinolin-8-yl)oxymethyl]-2,4-dichlorophenyl]sulfonyl]-N-[3-[[2-[4-(aminoiminomethyl)phenoxy]-1-oxoethyl]amino] propyl]-2(S)-pyrrolidinecarboxamide dihydrochloride The expected product (yield=96%) is obtained by following a procedure analogous to Example 6, starting from the compound obtained according to Example 9. M.p.= 168–172° C. $[\alpha]_D^{25}$==20° (c=0.3; $CH_3OH$)

PREPARATION I

1-[[3-[(2,4-Dimethylquinolin-8-yl)oxymethyl]-2,4-dichlorophenyl]sulfonyl]-N-[3-[(3-cyanophenyl) carbonylamino]propyl]-2(S)-pyrrolidinecarboxamide By following a procedure analogous to Example 5, starting from 3-cyanobenzoic acid, the expected product is obtained in the form of a white solid after purification by chromatography on silica gel using a dichloromethane/methanol mixture (98/2; v/v) as the eluent (yield=75%). M.p.=102–106° C. $[\alpha]_D^{24}$=−40° (c=0.33; $CH_3OH$)

PREPARATION II

1-[[3-[(2,4-Dimethylquinolin-8-yl)oxymethyl]-2, 4dichlorophenyl]sulfonyl]-N-[3-[[3-[(amino) (hydroxyimino)methyl]phenyl]carbonylamino] propyl]-2(S)-pyrrolidinecarboxamide A solution of 1.1 g (1.58.10$^{-3}$ mol) of the compound obtained according to Preparation I in 30 ml of dimethyl sulfoxide is prepared and 0.55 g (7.9.10$^{-3}$ mol) of hydroxylamine hydrochloride and then 0.8 g (7.9.10$^{-3}$ mol) of triethylamine are added. After stirring for two hours at room temperature, the same amounts of these two reagents are added again and stirring is continued for 4 hours. 200 ml of water are then added. The precipitate obtained is filtered off and redissolved in dichloromethane. The organic solution is washed with water, dried over sodium sulfate and then concentrated under reduced pressure to give 1.13 g of the expected product in the form of white crystals (yield=98%). M.p.=108–110° C. $[\alpha]_D^{24}$=−30° (c=0.38; $CH_3OH$)

PREPARATION III

1-[[3-[(2,4-Dimethylquinolin-8-yl)oxymethyl]-2,4-dichlorophenyl]sulfonyl]-N-[3-[[3-[(amino) (acetoxyimino)methyl]phenyl]carbonylamino] propyl]-2(S)-pyrrolidinecarboxamide 0.03 g (0.28.10$^{-3}$ mol) of acetic anhydride is added to a solution of 0.2 g (0.27.10$^{-3}$ mol) of the compound obtained according to Preparation II in 10 ml of anhydrous dichloromethane and the reaction mixture is stirred for 15 hours. About 50 ml of dichloromethane are added to the mixture and this organic phase is washed with water and then dried over sodium sulfate. After concentration under reduced pressure, 0.20 g of the expected product is obtained in the form of a white solid (yield=95%). M.p.=100–104° C. $[\alpha]_D^{24}$=−20° (c=0.29; $CH_3OH$)

EXAMPLE 11

1-[[3-[(2,4-Dimethylquinolin-8-yl)oxymethyl]-2,4-dichlorophenyl]sulfonyl]-N-[3-[[3-(aminoiminomethyl)phenyl]carbonylamino]propyl]-2(S)-pyrrolidine-carboxamide A solution of 0.2 g (0.26.10$^{-3}$ mol) of the compound obtained according to Preparation III in 5 ml of methanol is prepared and 10 mg of Lindlar's catalyst (containing 5% of palladium) are added. The mixture is stirred under a hydrogen atmosphere at atmospheric pressure, at room temperature, for 3 hours. After removal of the catalyst by filtration, the solution is concentrated under reduced pressure. The crude product obtained is purified by chromatography on $NH_2$-grafted silica gel (LICHROPREP® $NH_2$) using a dichloromethane/methanol mixture (95/5; v/v) as the eluent to give 0.11 g of the expected product in the form of a white solid (yield=55%). M.p.=116–120° C. $[\alpha]_D^{24}$=−36° (c=0.35; $CH_3OH$)

EXAMPLE 12

1-[[3-[[(2,4-Dimethylquinolin-8-yl)oxymethyl]-2,4-dichlorophenyl]sulfonyl]-N-[3-[[3-(aminoiminomethyl)phenyl]carbonylamino]propyl]-2(S)-pyrrolidine-carboxamide dihydrochloride The expected product (yield=98%) is obtained by following a procedure analogous to Example 8, starting from the compound obtained according to Example 11. M.p.= 192–194° C. $[\alpha]_D^{22}$=−31° (c=0.3; $CH_3OH$)

PREPARATION IV

N-Ethyl-N-(3-aminopropyl)carbamic acid 1, 1dimethylethyl ester

A solution of 3.42 g (0.017 mol) of N-ethyl-N-(2-cyanoethyl)carbamic acid 1,1-dimethylethyl ester in 70 ml of ethanol is prepared and 0.5 g of Raney nickel is added.

The mixture is stirred under a hydrogen atmosphere at atmospheric pressure, at room temperature, for 6 hours. The catalyst is filtered off and the filtrate is then concentrated under reduced pressure. The residual oil is then purified by chromatography on NH$_2$-grafted silica gel using a toluene/isopropanol mixture (95/5; v/v) as the eluent to give 1.72 g of the expected product in the form of a colorless oil (yield=50%). $^1$H NMR (300 MHz; CDCl$_3$) 1.09 (t, 3H); 1.28 (d, 2H); 1.46 (s, 9H); 1.64 (m, 2H); 2.67 (t, 2H); 3.25 (m, 4H)

PREPARATION V

1-[[3-[(2,4Dimethylquinolin-8-yl)oxymethyl]-2,4-dichlorophenyl]sulfonyl]-N-[3-[(ethyl)(1,1-dimethylethoxycarbonyl)amino]propyl]-2(S)-pyrrolidine-carboxamide A solution of 3.85 g (7.55.10$^{-3}$ mol) of 1-[[3-[(2,4-dimethylquinolin-8-yl)oxymethyl]-2,4-dichlorophenyl]sulfonyl]-L-proline in 20 ml of dichloromethane is prepared and 1.59 g (8.3.10$^{-3}$ mol) of EDCI, 1.13 g (8.3.10$^{-3}$ mol) of HOAT and then 1.68 g (8.3.10$^{-3}$ mol) of N-ethyl-N-(3-aminopropyl)carbamic acid 1,1-dimethylethyl ester are added. The reaction mixture is stirred for 24 hours at room temperature and then concentrated under reduced pressure. The residue is purified by chromatography on silica gel using a dichloromethane/methanol mixture (98/2; v/v) as the eluent to give 5 g of the expected product in the form of an amorphous, light yellow solid (yield=95%). M.p.=80° C. [α]$_D^{25}$=−34° (c=0.47; CH$_3$OH)

PREPARATION VI

1-[[3-[(2,4-Dimethylquinolin-8-yl)oxymethyl]-2,4-dichlorophenyl]sulfonyl]-N-[3-(ethylamino)propyl]-2(S)-pyrrolidinecarboxamide 3 ml of trifluoroacetic acid and 0.408 g (3.78.10$^{-3}$ mol) of anisole are added to a solution, cooled to 0° C. beforehand, of 2.62 g (3.78.10$^{-3}$ mol) of the compound obtained according to Preparation V in 8 ml of dichloromethane. The reaction mixture is stirred for 1 hour at 0° C. and then for 20 hours at room temperature. After removal of the solvent under reduced pressure, water is added to the residue and the pH of the aqueous phase is rendered basic with 1 N NaOH solution. After extraction with ethyl acetate, the organic phase is washed with water, dried over sodium sulfate and concentrated under reduced pressure to give 2.14 g of the expected product in the form of a beige solid (yield 95%). M.p.=70° C. [α]$_D^{25}$=−44° (c=0.38; CH$_3$OH)

EXAMPLE 13

1-[[3-[(2,4-Dimethylquinolin-8-yl)oxymethyl]-2,4dichlorophenyl]sulfonyl]-N-[3-[[ethyl]-[[4-(aminoiminomethyl)phenyl]carbonyl]amino]propyl]-2(S)-pyrrolidineacarboxamide A solution of 0.2 g (0.337.10$^{-3}$ mol) of the compound obtained according to Preparation VI in 10 ml of dichloromethane is prepared and 0.07 g (0.337.10$^{-3}$ mol) of 4-(aminoiminomethy)benzoyl chloride hydrochloride and 0.027 g (0.27.10$^{-3}$ mol) of N-methylmorpholine are added to the solution. The reaction mixture is stirred for 20 hours and then concentrated under reduced pressure. The residue is redissolved in water and the pH of the solution is rendered slightly alkaline with 1 N NaOH. After extraction with dichloromethane, the organic phase is washed with water, dried over sodium sulfate and concentrated under reduced pressure. The residue is purified by chromatography on NH$_2$-grafted silica using a dichloromethane/methanol mixture (95/5; v/v) as the eluent to give 0.12 g of the expected product in the form of a creamy white solid (yield=48%). M.p.=160° C.

EXAMPLE 14

1-[[3-[(2,4-Dimethylquinolin-8-yl)oxymethyl]-2,4-dichlorophenyl]sulfonyl]-N-3-[[ethyl]-[[4-(aminoiminomethyl)phenyl]carbonyl]amino]propyl]-2(S)-pyrrolidine carboxamide dihydrochloride The expected product (yield=80%) is obtained by following a procedure analogous to Example 8, starting from the compound obtained according to Example 13. M.p.=193° C. [α]$_D^{25}$=−27° (c=0.37; CH$_3$OH)

PREPARATION VII

1-[[3-[(2,4-Dimethylquinolin-8-yl)oxymethyl]-2,4-dichlorophenyl]sulfonyl]-N-[3-[(methyl)(1,1-dimethylethoxycarbonyl)amino]propyl]-2(S)-pyrrolidine carboxamide The product (yield=73%) is obtained by following a procedure analogous to Preparation V, starting from N-methyl-N-(3-aminopropyl)carbamic acid 1,1-dimethylethyl ester. M.p.=80° C. [α]$_D^{25}$=−40° (c=0.42; CH$_3$OH)

PREPARATION VIII

1-[[3-[(2,4-Dimethylquinolin-8-yl)oxymethyl]-2,4-dichlorophenyl]sulfonyl]-N-[3-(methylamino)propyl]-2(S)-pyrrolidinecarboxamide The expected product (yield=92%) is obtained by following a procedure analogous to Preparation VI, starting from the compound obtained according to Preparation VII. M.p.=85° C. [α]$_D^{25}$=−37° (c=0.39; CH$_3$OH)

EXAMPLE 15

1-[[3-[(2,4-Dimethylquinolin-8-yl)oxymethyl]-2,4-dichlorophenyl]sulfonyl]-N-[3-[[methyl]-[[4-(aminoiminomethyl)phenyl]carbonyl]amino]propyl]-2(S)-pyrrolidinecarboxamide The expected product (yield=51%) is obtained by following a procedure analogous to Example 13, starting from the compound obtained according to Preparation VIII. M.p.=158° C. [α]$_D^{25}$=−29° (c=0.55; CH$_3$OH)

EXAMPLE 16

1-[[3-[(2,4-Dimethylquinolin-8-yl)oxymethyl]-2,4-dichlorophenyl]sulfonyl]-N-[3-[[methyl]-[[4 (aminoiminomethyl)phenyl]carbonyl]amino]propyl]-2(S)-pyrrolidinecarboxamide dihydrochloride The expected product (yield=76%) is obtained by following a procedure analogous to Example 8, starting from the compound obtained according to Example 15. M.p.=196° C. [α]$_D^{25}$=−29° (c=0.36; CH$_3$OH)

PREPARATION IX

1-[[3-[(2-Methylquinolin-8-yl)oxymethyl]-2,4-dichlorophenyl]sulfonyl]-N-[3-[(4-cyanophenyl)carbonylamino]propyl]-2(S)-pyrrolidinecarboxamide By following a procedure analogous to Example 5, starting from 4-cyanobenzoic acid and 1-[[3-[(2-methylquinolin- 8-yl)oxymethyl]-2,4-dichlorophenyl]sulfonyl]-N-[3-aminopropyl]-2(S)-pyrrolidinecarboxamide hydrochloride, the expected product (yield=75%) is obtained after purification by chromatography on silica gel using a dichloromethane/methanol mixture (98/2; v/v) as the eluent. M.p.=78–80° C. $[\alpha]_D^{24}$=–39° (c=0.3; $CH_3OH$)

PREPARATION X

1-[[3-[(2-Methylquinolin-8-yl)oxymethyl]-2,4-dichlorophenyl]sulfonyl]-N-[3-[[4-[(amino)(hydroxyimino)methyl]phenyl]carbonylamino]propyl]-2(S)-pyrrolidinecarboxamide The expected product (yield=70%) is obtained by following a procedure analogous to Preparation II, starting from the compound obtained according to Preparation IX. M.p.= 120–124° C. $[\alpha]_D^{24}$=–35° (c=0.3; $CH_3OH$)

PREPARATION XI

1-[[3-[(2-Methylquinolin-8-yl)oxymethyl]-2,4-dichlorophenyl]sulfonyl]-N-[3-[[4-[(amino)(acetoxyimino)methyl]phenyl]carbonylamino]propyl]-2(S)-pyrrolidinecarboxamide The expected product (yield=72%) is obtained by following a procedure analogous to Preparation III, starting from the compound obtained according to Preparation X.

M.p.=122–126° C.

$[\alpha]_D^{24}$=–36° (c=0.27; $CH_3OH$)

EXAMPLE 17

1-[[3-[(2-Methylquinolin-8-yl)oxymethyl]-2,4-dichlorophenyl]sulfonyl]-N-[3-[[4-(aminoiminomethyl)phenyl]carbonylamino]propyl]-2(S)-pyrrolidinecarboxamide The expected product (yield=76%) is obtained by following a procedure analogous to Example 11, starting from the compound obtained according to Preparation XI.

M.p.=118–120° C.

$[\alpha]_D^{24}$=–38° (c=0.35; $CH_3OH$)

EXAMPLE 18

1-[[3-[(2-Methylquinolin-8-yl)oxymethyl]-2,4-dichlorophenyl]sulfonyl]-N-[3-[[4-(aminoiminomethyl)phenyl]carbonylamino]propyl]-2(S)-pyrrolidinecarboxamide dihydrochloride The expected product (yield=97%) is obtained by following a procedure analogous to Example 8, starting from the compound obtained according to Example 17.

M.p.=186–188° C.

$[\alpha]_D^{23}$=–37° (c=0.3; $CH_3OH$)

EXAMPLE 19

1-[[3-[(2,4-Dimethylquinolin-8-yloxymethyl]-2,4-dichlorophenyl]sulfonyl]-N-[4-[[4-(aminoiminomethyl)phenyl]carbonylamino]butyl]-2(S)-pyrrolidinecarboxamide dihydrochloride A solution of 0.34 g (1.69.10$^{-3}$ mol) of 4-(aminoiminomethyl)benzoic acid hydrochloride in 5 ml of dimethylformamide (DMF) is prepared and 0.46 g (1.69.10$^{-3}$ mol) of EDCI and 0.32 g (1.69.10$^{-3}$ mol) of HOAT are added. The mixture is stirred for 30 minutes at room temperature. The solution obtained is then added dropwise to a solution of 1 g (1.53.10$^{-3}$ mol) of 1-[[3-[(2,4-dimethylquinolin-8-yl)oxymethyl]-2,4-dichlorophenyl]sulfonyl]-N-[4-aminobutyl]-2(S)-pyrrolidinecarboxamide (in the form of the dihydrochloride) in 5 ml of DMF and 0.46 g (4.6.10$^{-3}$ mol) of triethylamine. The reaction mixture is stirred for 4 hours at room temperature and then poured into iced water. 1 N NaOH solution is added slowly to bring the pH to 8 and the mixture is extracted several times with dichloromethane. The combined organic phases are washed with water, dried over sodium sulfate and then concentrated under reduced pressure. The crude product is purified by chromatography a first time on $NH_2$-grafted silica gel using a dichloromethane/methanol mixture (98/2; v/v) as the eluent, and a second time on C18-grafted silica gel (type RP18) using a mixture of dichloromethane and 0.2 N HCl gas in methanol (98/2; v/v) as the eluent. After removal of the solvents under reduced pressure, the product is dissolved in 5 ml of distilled water and the solution is lyophilized to give 150 mg of the expected product in the form of a pale yellow solid (yield=13%).

M.p.=196–200° C.

$[\alpha]_D^{26}$=–20° (c 0.285; $CH_3OH$)

PREPARATION XII

1-[[3-[(2,4-Dimethylquinolin-8-yl)oxymethyl]-2,4-dichlorophenyl]sulfonyl]-N-[5-[(1,1-dimethylethoxycarbonyl)amino]pentyl]-2(S)-pyrrolidinecarboxamide The expected product (yield=43%) is obtained by following a procedure analogous to Preparation V, starting from (5-aminopentyl)carbamic acid 1,1-dimethylethyl ester.

M.p.=78–82° C.

PREPARATION XIII

[1-[[3-[(2,4-Dimethylquinolin-8-yl)oxymethyl]-2,4-dichlorophenyl]sulfonyl]-N-(5-aminopentyl)-2(S)-pyrrolidinecarboxamide dihydrochloride 2.9 g (4.2.10$^{-3}$ mol) of the compound obtained according to Preparation XII are added to 25 ml of 1 N hydrochloric acid solution and the mixture is stirred at 50° C. for 3 hours. The reaction medium is then cooled to 15° C. and washed with ethyl acetate. The aqueous phase is concentrated under reduced pressure and then taken up with 50 ml of distilled water. The solution is filtered and then lyophilized to give the expected product in the form of a white solid (yield=90%).

M.p.=162–166° C.

$[\alpha]_D^{24}$=–29° (c=0.31; $CH_3OH$)

EXAMPLE 20

1-[[3-[(2,4-Dimethylquinolin-8-yl)oxymethyl] 2,4-dichlorophenyl]sulfonyl]-N-[5-[[4-(aminoiminomethyl)phenyl]carbonylamino]pentyl]-2(S)-pyrrolidinecarboxamide The expected product (yield=30%) is obtained by following a procedure analogous to Example 1, starting from the compound obtained according to Preparation XIII.

M.p.=150–152° C.

$[\alpha]_D^{24}$=–14° (c=0.32; $CH_3OH$)

EXAMPLE 21

1-[[3-[(2,4-Dimethylquinolin-8-yl)oxymethyl]-2,4-dichlorophenyl]sulfonyl]-N-[5-[[4-(aminoiminomethyl)phenyl]carbonylamino]pentyl]-2(S)-pyrrolidinecarboxamide dihydrochloride The expected product (yield=97%) is obtained by following a procedure analogous to Example 8, starting from the compound obtained according to Example 20.

M.p.=182–185° C.
$[\alpha]_D^{25}$=–15° (c=0.31; $CH_3OH$)

PREPARATION XIV

N-(Methyl)-N-[3-[(4-cyanophenyl)carbonylamino] propyl]carbamic acid 1,1-dimethylethyl ester A solution of 1.23 g (6.53.10$^{-3}$ mol) of N-methyl-N-[3-aminopropyl]-carbamic acid 1,1-dimethylethyl ester in 10 ml of dichloromethane and 5 ml of pyridine is prepared and 1.08 g (6.53.10$^{-3}$ mol) of 4-cyanobenzoyl chloride are added. After stirring for 20 hours at room temperature, dichloromethane is added and this organic phase is washed with water, then with 1 N hydrochloric acid solution and then with water again. After drying over magnesium sulfate, the organic phase is concentrated under reduced pressure. The residue obtained is purified by chromatography on silica gel using a toluene/ethyl acetate mixture (8/2; v/v) as the eluent to give 1 g of the expected product in the form of a creamy white solid (yield=48%).
M.p.<50° C.

PREPARATION XV

4-Cyano-N-[3-(methylamino)propyl]benzamide

The expected product is obtained in the form of a light yellow oil (yield=89%) by following a procedure analogous to Preparation VI, starting from the compound obtained according to Preparation XIV.

$^1$H NMR (DMSO)
1.70 (q, 2H); 2.34 (s, 3H); 2.61 (t, 3H); 3.3 (m, 3H); 7.97 (s, 4H); 8.83 (bs, 1H)

PREPARATION XVI

1-[[3-[(2,4-Dimethylquinolin-8-yl)oxymethyl]-2,4-dichlorophenyl]sulfonyl]-N-[methyl]-N-[3-[(4-cyanophenyl)carbonylamino]propyl]-2(S)-pyrrolidinecarboxamide The expected product (yield=40%) is obtained by following a procedure analogous to Preparation V, starting from the compound obtained according to Preparation XV.
M.p.=100° C.
$[\alpha]_D^{19}$=–30° (c=0.32; $CH_3OH$)

PREPARATION XVII

1-[[3-[(2,4-Dimethylquinolin-8-yl)oxymethyl -2,4-dichlorophenyl]sulfonyl]-N-[methyl]-N-[3-[[4-[amino(hydroxyimino)methyl]phenyl] carbonylamino]-propyl]-2(S)-pyrrolidinecarboxamide The expected product (yield=95%) is obtained by following a procedure analogous to Preparation II, starting from the compound obtained in Preparation XVI.
M.p.=65–70° C.
$[\alpha]_D^{18}$=+18° (c =0.25; $CH_3OH$)

PREPARATION XVIII

1-[[3-[(2,4-Dimethylquinolin-8-yl)oxymethyl]-2,4-dichlorophenyl]sulfonyl]-N-[methyl]-N-[3-[[4-[amino(acetoxyimino)methyl]phenyl] carbonylamino]-propyl]-2(S)-pyrrolidinecarboxamide The expected product (yield=87%) is obtained by following a procedure analogous to Preparation III, starting from the compound obtained in Preparation XVII.

M.p.=70° C.
$[\alpha]_D^{19}$=–4.3° (c=0.32; $CH_3OH$)

EXAMPLE 22

1-[[3-[(2,4-Dimethylquinolin-8-yl)oxymethyl]-2,4-dichlorophenyl]sulfonyl]-N-[methyl]-N-[3-[[4-(aminoiminomethyl)phenyl]carbonylamino]propyl]-2(S)-pyrrolidinecarboxamide The expected product (yield=73%) is obtained by following a procedure analogous to Example 11, starting from the compound obtained in Preparation XVIII.
M.p.=133° C.
$[\alpha]_D^{19}$=–40° (c=0.33; $CH_3OH$)

EXAMPLE 23

1-[[3-[(2,4-Dimethylquinolin-8-yl)oxymethyl]-2,4-dichlorophenyl]sulfonyl]-N-[methyl]-N-[3-[[4-(aminoiminomethyl)phenyl]carbonylamino]propyl]-2(S)-pyrrolidinecarboxamide dihydrochloride A solution of 0.15 g (0.20.10$^{-3}$ mol) of the compound obtained according to Example 22 in 5 ml of anhydrous methanol is prepared and 1 ml of ethyl ether saturated with hydrogen chloride is added. The mixture is stirred for 10 minutes and 20 ml of ethyl ether are then added. The precipitate obtained is filtered off, rinsed with ether and redissolved in 5 ml of distilled water. After lyophilization of the solution, 0.15 g of the expected product is obtained in the form of a yellowish white solid (yield=91%).
M.p.=211° C.
$[\alpha]_D^9$=–8° (c=0.32; $CH_3OH$)

PREPARATION XIX

1-[[3-[(2,4-Dimethylquinolin-8-yl)oxymethyl]-2,4-dichlorophenyl]sulfonyl]-N-[methyl]-N-[3-[(methyl)(1,1-dimethylethoxycarbonyl)amino]propyl]-2(S)-pyrrolidinecarboxamide The expected product (yield=78%) is obtained by following a procedure analogous to Preparation VII, starting from N-methyl-N-[3-(methylamino)propyl]carbamic acid 1,1-dimethylethyl ester.
M.p.=50° C.
$[\alpha]_D^<$=–17° (c=0.38; $CH_3OH$)

PREPARATION XX

1-[[3-[(2,4-Dimethylquinolin-8-yl)oxymethyl]-2,4-dichlorophenyl]sulfonyl]-N-[methyl]-N-[3-(methylamino)propyl]-2(S)-pyrrolidinecarboxamide The expected product (yield=99%) is obtained by following a procedure analogous to Preparation VIII, starting from the compound obtained according to Preparation XIX.
M.p.=150° C.
$[\alpha]_D^{21}$=–26° (c=0.33; $CH_3OH$)

PREPARATION XXI

1-[[3-[(2,4-Dimethylquinolin-8-yl)oxymethyl]-2,4-dichlorophenyl]sulfonyl]-N-[methyl]-N[3-[(methyl)[(4-cyanophenyl)carbonyl]amino]propyl]-2(S)-pyrrolidinecarboxamide The expected product (yield=90%) is obtained by following a procedure analogous to Preparation I, starting from the compound obtained according to Preparation XX and 4-cyanobenzoic acid.

M.p.=60° C.

$[\alpha]_D^{21}$=+6° (c=0.72; CH$_3$OH)

PREPARATION XXII

1-[[3-[(2,4-Dimethylquinolin-8-yl)oxymethyl]-2,4-dichlorophenyl]sulfonyl]-N-[methyl]-N-[3-[(methyl) [[4-[amino(hydroxyimino)methyl]phenyl]carbonyl]-amino]propyl]-2(S)-pyrrolidinecarboxamide The expected product is obtained in the form of an oily product (yield=77%) by following a procedure analogous to Preparation II, starting from the compound obtained in Preparation XXI.

$n_D^{23}$=1.571

$[\alpha]_D^{21}$=−18° (c=0.55; CH$_3$OH)

PREPARATION XXIII

1-[[3-[(2,4-Dimethylquinolin-8-yl)oxymethyl]-2,4-dichlorophenyl]sulfonyl]-N-[methyl]-N-[3-[(methyl) [[4-(amino(acetoxyimino)methyl]phenyl]carbonyl]-amino]propyl]-2(S)-pyrrolidinecarboxamide The expected product (yield=60%) is obtained by following a procedure analogous to Preparation III, starting from the compound obtained in Preparation XXIII.

M.p.=70° C.

$[\alpha]_D^{21}$=−12° (c=0.45; CH$_3$OH)

EXAMPLE 24

1-[[3-[(2,4-Dimethylquinolin-8-yl)oxymethyl]-2,4-dichlorophenyl]sulfonyl]-N-[methyl]-N-[3-[(methyl) [[4-(aminoiminomethyl)phenyl]carbonyl]amino]-propyl]-2(S)-pyrrolidinecarboxamide The expected product (yield=72%) is obtained by following a procedure analogous to Example 11, starting from the compound obtained in Preparation XXIII.

M.p.=170° C.

$[\alpha]_D^{21}$=−16.2° (c=0.69; CH$_3$OH)

EXAMPLE 25

1-[[3-[(2,4-Dimethylquinolin-8-yl)oxymethyl]-2,4-dichlorophenyl]sulfonyl]-N-[methyl]-N-[3-[(methyl) [[4-(aminoiminomethyl)phenyl]carbonyl]amino]-propyl]-2(S) pyrrolidinecarboxamide dihydrochloride The expected product (yield=86%) is obtained by following a procedure analogous to Example 8, starting from the compound obtained in Example 22.

M.p.=175° C.

$[\alpha]_D^2$=−2.4° (c=0.38; CH$_3$OH)

PREPARATION XXIV

1-[[3-[(2,4-Dimethylquinolin-8-yloxymethyl]-2,4-dichlorophenyl]sulfonyl]-N-[3-[(5-cyanopyridin-2-yl)carbonylamino]propyl]-2(S)-pyrrolidinecarboxamide A suspension of 1.90 g (10.3.10$^{-3}$ mol) of 5-cyanopicolinic acid hydrochloride in 50 ml of dichloromethane is prepared and 1.10 ml (34.10$^{-3}$ mol) of N-methylmorpholine are added. After stirring for 30 min, 1.68 g (12.3.10$^{-3}$ mol) of HOAT and then 2.37 g (12.3.10$^{-3}$ mol) of EDCI are added. The mixture is stirred for 1 hour at room temperature and 6.65 g (10.3.10$^{-3}$ mol) of 1-[[3-[(2,4-dimethylquinolin-8-yl)oxymethyl]-2,4-dichlorophenyl] sulfonyl]-N-[3-aminopropyl]-2(S)-pyrrolidinecarboxamide hydrochloride and 2.55 ml (72.10$^{-3}$ mol) of N-methylmorpholine dissolved in 30 ml of dichloromethane are then added dropwise. After stirring overnight at room temperature, the reaction mixture is poured into 100 ml of water and then extracted twice with dichloromethane. The combined organic phases are washed with water, dried over magnesium sulfate and concentrated under reduced pressure. The crude product obtained (3.16 g) is purified by chromatography on silica gel using ethyl acetate as the eluent to give 2.18 g of the expected product in the form of light yellow crystals (yield=30.4%).

M.p.=91–93° C.

$[\alpha]_D^{20}$=−39° (c=0.99; CH$_3$OH)

PREPARATION XXV

1-[[3-[(2,4-Dimethylquinolin-8-yl)oxymethyl]-2,4-dichlorophenyl]sulfonyl]-N-[3-[[5-[(amino) (hydroxyimino)methyl]pyridin-2-yl]carbonylamino] propyl]-2(S)-pyrrolidinecarboxamide The expected product is obtained in the form of pale yellow crystals (yield=72%) by following a procedure analogous to Preparation II, starting from the compound obtained according to Preparation XXIV.

M.p.=134–136° C.

$[\alpha]_D^{21}$=−32° (c=1.00; CH$_3$OH)

PREPARATION XXVI

1-[[3-[(2,4-Dimethylquinolin-8-yl)oxymethyl]-2,4-dichlorophenyl]sulfonyl]-N-[3-[[5-[(amino) (acetoxyimino)methyl]pyridin-2-yl]carbonylamino] propyl]-2(S)-pyrrolidinecarboxamide The expected product is obtained in the form of creamy white crystals (yield=92%) by following a procedure analogous to Preparation III, starting from the compound obtained according to Preparation XXV.

M.p.=116–118° C.

$[\alpha]_D^{22}$=−13° (c=1.05; CH$_3$OH)

EXAMPLE 26

1-[[3-[(2,4-Dimethylquinolin-8-yl)oxymethyl]-2,4-dichlorophenyl]sulfonyl]-N-[3-[[5-(aminoiminomethyl)pyridin-2-yl]carbonylamino] propyl]-2(S)-pyrrolidinecarboxamide The expected product is obtained in the form of white crystals (yield=65%) by following a procedure analogous to Example 11, starting from the compound obtained according to Preparation XXVI.

M.p.=145–147° C.

$[\alpha]_D^{22}$=−36° (c=1.03; CH$_3$OH)

EXAMPLE 27

1-[[3-[(2,4-Dimethylquinolin-8-yl)oxymethyl]-2,4-dichlorophenyl]sulfonyl]-N-[3-[[5-(aminoiminomethyl)pyridin-2-yl]carbonylamino] propyl]-2(S)-pyrrolidinecarboxamide di (methanesulfonate)

A solution of 0.64 g (0.9.10$^{-3}$ mol) of the compound obtained according to Example 26 in 12.5 ml of methanol is prepared and 86.3 mg of methanesulfonic acid are added. The mixture is stirred for one hour at room temperature and then poured into 700 ml of ethyl ether, with stirring. The precipitate obtained is filtered off, washed with ether and then redissolved in 60 ml of water. The solution obtained is filtered and lyophilized to give 0.675 g of the expected product in the form of white flakes (yield=92%).

M.p.=160° C. (decomposition)

$[\alpha]_D^{21}$=−21° (c=1.03; $CH_3OH$)

PREPARATION XXVII

3-[[1-[[3-[(2,4-Dimethylquinolin-8-yl)oxymethyl]-2,4-dichlorophenyl]sulfonyl]-pyrrolidin-2-yl]carbonylamino]propionic acid methyl ester A mixture of 6.85 g ($13.4.10^{-3}$ mol) of N-[[3-[(2,4-dimethylquinolin-8 -yl)oxymethyl]-2,4-dichlorophenyl]sulfonyl]-L-proline, 2.01 g ($14.7.10^{-3}$ mol) of HOAT and 2.83 g ($14.7.10^{-3}$ mol) of EDCI in 50 ml of dimethylformamide is prepared. After stirring for 15 min at room temperature, this mixture is added dropwise to a solution of 2.06 g of methyl 4-aminobutyrate (in the form of the hydrochloride) in 35 ml of dimethylformamide and 1.48 ml ($13.4.10^{-3}$ mol) of N-methylmorpholine. The reaction mixture is stirred for 20 hours at room temperature and 500 ml of dichloromethane are then added, followed by 300 ml of water. After decantation, the organic phase is washed twice with water again, dried over sodium sulfate and then concentrated under reduced pressure. The crude product obtained is purified by chromatography on silica gel using a cyclohexane/ethyl acetate mixture (3/7; v/v) as the eluent to give 5.3 g of the expected product in the form of yellow crystals (yield=64.5%).

M.p.=64–67° C.

$[\alpha]_D^{24}$=−40.4° (c=1.10; $CH_2Cl_2$)

PREPARATION XXVIII

3-[[1-[[3-[(2,4-Dimethylquinolin-8-yl)oxymethyl]-2,4-dichlorophenyl]sulfonyl]-pyrrolidin-2-yl]carbonylamino]propionic acid hydrochloride A mixture of 5.07 g of the compound obtained according to Preparation XXII with 9.1 ml of 1 N aqueous sodium hydroxide solution is heated at 90–100° C. for 1 hour. After cooling, 30 ml of water are added and the aqueous phase is extracted twice with 50 ml of ethyl acetate and then acidified to pH 1 with 1 N hydrochloric acid solution. The insoluble product is redissolved in dichloromethane and the organic phase is washed with a small amount of water, dried over sodium sulfate and concentrated under reduced pressure to give 2.8 g of the expected product in the form of white crystals (yield=53%).

M.p.=146–148° C.

$[\alpha]_D^{24}$=−21.2° (c=1.00; $CH_3OH$)

EXAMPLE 28

1-[[3-[(2,4-Dimethylquinolin-8-yl)oxymethyl]-2,4-dichlorophenyl]sulfonyl]-N-[3-[[4-(aminoiminomethyl)phenyl]methylaminocarbonyl]propyl]-2(S)-pyrrolidinecarboxamide A solution of 2 g ($1.58.10^{-3}$ mol) of the acid obtained according to Preparation XXVIII in 20 ml of dimethylformamide is prepared and 0.364 g ($1.89.10^{-3}$ mol) of EDCI and 0.723 g ($1.89.10^{-3}$ mol) of HATU [O-(7-azabenzotriazol-1-yl)-1,1,3,3-tetramethyluronium hexafluorophosphate] are added. After stirring for 30 min, 0.52 ml ($4.7.10^{-3}$ mol) of N-methylmorpholine and then 0.352 g ($1.58.10^{-3}$ mol) of 4-(aminoiminomethyl) phenylmethanamine dihydrochloride are added. The reaction mixture is stirred for 16 hours at room temperature and 150 ml of ethyl ether are then added. The precipitate formed is filtered off, washed with water, then with 10 ml of 1 N sodium hydroxide solution and then with water again and dried in a desiccator. The resulting crude product is purified by chromatography on $NH_2$-grafted silica gel using a dichloromethane/ethanol mixture (95/5; v/v) as the eluent to give 0.21 g of the expected product in the form of white crystals (yield=18%).

M.p.=112–114° C.

$[\alpha]_D^{23}$=−24° (c=0.64; $CHCl_3$)

EXAMPLE 29

1-[[3-[(2,4-Dimethylquinolin-8-yl)oxymethyl]-2,4-dichlorophenyl]sulfonyl]-N-[3-[[4-(aminoiminomethyl)phenyl]methylaminocarbonyl]propyl]-2(S)-pyrrolidinecarboxamide hydrochloride A solution of 0.169 g ($0.23.10^{-3}$ mol) of the compound obtained according to Example 28 in 8 ml of dichloromethane is prepared and 0.23 ml of a solution containing 1 mol/l of hydrogen chloride in ethyl ether is added. After stirring for one hour at room temperature, the mixture is concentrated under reduced pressure. The residue is taken up with ethyl ether and filtered off. The solid obtained is washed with ether and then redissolved in 20 ml of water. The solution obtained is filtered and lyophilized to give 0.16 g of the expected product in the form of white crystals (yield=90%).

M.p.=178–180° C.

$[\alpha]_D^{27}$=−3.5° (c=0.96; $C_2H_5OH$)

EXAMPLE 30

1-[[3-[(2,4-Dimethylquinolin-8-yl)oxymethyl]-2,4-dichlorophenyl]sulfonyl]-N-[3-[[4-(aminoiminomethyl)phenyl]aminocarbonyl]propyl]-2(S)-pyrrolidinecarboxamide The expected product is obtained in the form of white crystals (yield=10%) by following a procedure analogous to Example 28, starting from the acid obtained according to Preparation XXVIII and 4-(aminoiminomethyl)aniline.

M.p.=140–141° C.

EXAMPLE 31

1-[[3-[(2,4-Dimethylquinolin-8-yl)oxymethyl]-2,4-dichlorophenyl]sulfonyl]-N-[3-[[4-(aminoiminomethyl)phenyl]aminocarbonyl]propyl]-2(S)-pyrrolidinecarboxamide hydrochloride The expected product is obtained in the form of white crystals (yield=90%) by following a procedure analogous to Example 29, starting from the compound obtained according to Example 30.

M.p.=192–193° C.

PREPARATION XXIX

4-[(2-Methoxyphenyl)imino]-1,1,1-trifluoro-2-pentanone

A mixture of 28.4 g (0.23 mol) of 2-methoxyaniline and 43.2 g (0.28 mol) of 1,1,1-trifluoro-2,4-pentanedione is prepared and heated at 100–105° C. for 1 h, with stirring. After cooling, the reaction mixture is redissolved in ethyl ether and the solution obtained is dried over sodium sulfate and then concentrated under reduced pressure to give 59.1 g of the expected product in the form of a beige solid (yield=99%).

M.p.=40° C.

PREPARATION XXX

8-Methoxy-2-methyl-4-(trifluoromethyl)quinoline 10 g ($38.10^{-3}$ mol) of the compound obtained according to Preparation XXIX are mixed with 50 g of polyphosphoric acid and the mixture is heated at 165° C. for 3 hours, with stirring. After cooling, the reaction medium is poured into iced water. The mixture obtained is extracted with ethyl ether and the organic phase is washed with sodium bicarbonate solution, with dilute hydrochloric acid solution and then with water. After drying of the organic phase and concentration under reduced pressure, 5.2 g of the expected product are obtained in the form of a cream-colored solid (yield=56%).

M.p.=112–113° C.

PREPARATION XXXI

8-Hydroxy-2-methyl-4-(trifluoromethyl)quinoline

A solution of 6.15 g (25.5. $10^{-3}$ mol) of the compound obtained according to Preparation XXX in 200 ml of dichloromethane is cooled to −60° C. and 130 ml of a 1 M solution of boron tribromide in dichloromethane are added dropwise, with stirring. The reaction medium is allowed to return to room temperature and stirred for 12 hours. The mixture is cooled to −60° C. and 140 ml of methanol are added slowly. It is then allowed to return to room temperature and stirred for 2 hours. The mixture is then concentrated under reduced pressure and the residue is taken up with dichloromethane. The organic phase is washed with sodium bicarbonate solution and then with water, and then dried over sodium sulfate and concentrated under reduced pressure to give 5.60 g of the expected product in the form of a yellow solid (yield=96%).

M.p.=60–61° C.

PREPARATION XXXII

N-[[3-[[2-Methyl-4-(trifluoromethyl)quinolin-8-yl]oxymethyl]-2,4-dichlorophenyl]sulfonyl]-L-proline methyl ester A solution of 1.08 g ($4.8.10^{-3}$ mol) of the compound obtained according to Preparation XXXI in 20 ml of dimethylformamide is prepared and 0.156 g ($5.2.10^{-3}$ mol) of sodium hydride as an 80% suspension in oil is added. After stirring for one hour at room temperature, 2.05 g ($4.8.10^{-3}$ mol) of N-[(3-bromomethyl-2,4-dichlorophenyl)sulfonyl]-L-proline methyl ester dissolved in 25 ml of dimethylformamide are added. The reaction mixture is stirred for 24 hours at room temperature and 250 ml of water are then added slowly. The mixture is extracted several times with ethyl ether and the combined organic phases are washed with water, dried and then concentrated under reduced pressure. The crude product obtained is purified by chromatography on silica gel using a cyclohexane/ethyl acetate mixture (70/30; v/v) as the eluent to give 1.23 g of the expected product in the form of a white solid (yield=45%).

M.p.=164–165° C.
$[\alpha]_D^{21}$=−16° (c=1.00; $CH_2Cl_2$)

PREPARATION XXXIII

N-[[3-[[2-Methyl-4-(trifluoromethyl)quinolin-8-yl]oxymethyl]-2,4-dichlorophenyl]sulfonyl]-L-proline A solution of 1.08 g ($1.9.10^{-3}$ mol) of the ester obtained according to Preparation XXXII in 10 ml of methanol and 10 ml of 1 N aqueous sodium hydroxide solution is prepared, the mixture is heated at 90–100° C. for 2 hours, with stirring, and the reaction medium is then concentrated under reduced pressure. The residue is taken up with water, ethyl ether is added and the mixture is acidified to pH 2.5 with dilute hydrochloric acid solution. After decantation and extraction of the aqueous phase with ethyl ether, the combined organic phases are washed with water, dried and then concentrated under reduced pressure. After purification by chromatography on silica gel using an ethyl acetate/methanol mixture (90/10; v/v) as the eluent, 0.95 g of the expected product is obtained in the form of a cream-colored powder (yield=90%).

M.p.=215° C.
$[\alpha]_D^{25}$=−2.3° (c=0.78; DMSO)

PREPARATION XXXIV

[3-[(4-Cyanobenzoyl)amino]propyl]carbamic acid 1,1-dimethylethyl ester

A solution of 10 g ($57.10^{-3}$ mol) of (3-aminopropyl)carbamic acid 1,1-dimethylethyl ester (or N-Boc-1,3-propanediamine) in 75 ml of dichloromethane is prepared and 15.9 ml ($114.10^{-3}$ mol) of triethylamine are added. The mixture is cooled with an ice bath and 10.38 g ($60.10^{-3}$ mol) of 4-cyanobenzoyl chloride are added gradually. The reaction medium is allowed to return to room temperature, stirred for 10 hours and then poured into 150 ml of water. The mixture is extracted with dichloromethane and the organic phase obtained is washed with 1 N hydrochloric acid solution and then with water and finally dried over sodium sulfate and concentrated under reduced pressure to give 16.4 g of the expected product in the form of ochre crystals (yield=94%).

$^1$H NMR (DMSO) 1.37 (s, 9H); 1.63 (m, 2H); 2.97 (m, 2H); 3.26 (m, 2H); 6.84 (t, lH); 7.97 (s, 4H); 8.70 (t, 1)

PREPARATION XXXV

N-(3-Aminopropyl)-4-cyanobenzamide hydrochloride 16.4 g ($54.10^{-3}$ mol) of the compound obtained according to Preparation III are dissolved in 150 ml of ethyl acetate, and 104 ml of a solution containing 2.6 mol/l of hydrogen chloride in ethyl acetate are then added. The mixture is stirred at room temperature for 24 hours and then concentrated under reduced pressure. The resulting crude product is washed with ethyl ether and dried under vacuum at 40° C. to give 12.15 g of the expected product in the form of an off-white solid (yield=94%).

M.p.=176–180° C.

PREPARATION XXXVI

1-[[3-[[2-Methyl-4-(trifluoromethyl)quinolin-8-yl]oxymethyl]-2,4-dichlorophenyl]sulfonyl]-N-[3-[(4-cyanophenyl)carboxy]amino]propyl]-2(S)-pyrrolidinecarboxamide The expected product is obtained in the form of white crystals (yield=53%) by following a procedure analogous to Preparation V, starting from the compounds obtained according to Preparations XXXII and XXXV and in the presence of N-methylmorpholine.

M.p.=92–94° C.

$[\alpha]_D^{24}$=−30° (c=1.01; CHCl$_3$)

PREPARATION XXXVII

1-[[3-[[2-Methyl-4-(trifluoromethyl)quinolin-8-yl] oxymethyl]-2,4-dichlorophenyl]sulfonyl]-N-[3-[[4-[(amino)(hydroxyimino)methyl]phenyl] carbonylamino]propyl]-2(S)-pyrrolidinecarboxamide The expected product is obtained in the form of yellow crystals (yield=16%) by following a procedure analogous to Preparation II, starting from the compound obtained according to Preparation XXXVI.

M.p.=192–194° C.

$[\alpha]_D^{22}$=−11° (c=1.00; DMSO)

PREPARATION XXXVIII

1-[[3-[[2-Methyl-4-(trifluoromethyl)quinolin-8-yl] oxymethyl]-2,4-dichlorophenyl]sulfonyl]-N-[3-[[4-[(amino)(acetoxyimino)methyl]phenyl] carbonylamino]propyl]-2(S)-pyrrolidinecarboxamide The expected product is obtained in the form of white crystals (yield=96%) by following a procedure analogous to Preparation III, starting from the compounds obtained according to Preparation XXXVII.

M.p.=170–172° C.

$[\alpha]_D^{24}$=−13° (c=0.49; DMSO)

EXAMPLE 32

1-[[3-[[2-Methyl-4-(trifluoromethyl)quinolin-8-yl] oxymethyl]-2,4-dichlorophenyl]sulfonyl]-N-[3-[[4-(aminoiminomethyl)phenyl]carbonylamino]propyl]-2(S)-pyrrolidinecarboxamide The expected product is obtained in the form of a pale yellow solid (yield=70%) by following a procedure analogous to Example 11, starting from the compounds obtained according to Preparation XXXVIII.

M.p.=142–144° C.

$[\alpha]_D^{24}$=−35 (c=0.95; CH$_3$OH)

EXAMPLE 33

1-[[3-[[2-Methyl-4-(trifluoromethyl)quinolin-8-yl] oxymethyl]-2,4-dichlorophenyl]sulfonyl]-N-[3-[[4-(aminoiminomethyl)phenyl]carbonylamino]propyl]-2(S)-pyrrolidinecarboxamide methanesulfonate The expected product is obtained, after lyophilization, in the form of pale yellow flakes (yield=97%) by following a procedure analogous to Example 27, starting from the compound obtained according to Example 32.

M.p.=150–154° C.

$[\alpha]_D^{21}$=−33.5° (c=0.98; CH$_3$OH)

PREPARATION XXXIX 2,6-Dimethyl-3-(chlorosulfonyl)benzoic acid 4 ml of chlorosulfonic acid are added slowly to 1 g (0.067 mol) of 2,6-dimethylbenzoic acid and the reaction mixture is stirred for 1 hour at 55° C. After cooling, the mixture is poured into 100 ml of iced water. The precipitate formed is filtered off, washed with cold water and then dried in a desiccator under vacuum to give 1.22 g of the expected product in the form of a white solid (yield=73%).

M.p.=146° C.

PREPARATION XL 2,6-Dimethyl-3-[[2(S)-(methoxycarbonyl)pyrrolidin-1-yl]sulfonyl]benzoic acid The expected product is obtained in the form of a cream-colored solid (yield=32%) by following a procedure analogous to Preparation XIV, starting from the acid chloride obtained according to Preparation XXXIX and L-proline methyl ester.

M.p.=110° C.

$[\alpha]_D^{29}$=−30.5° (c 0.60; CH$_3$OH)

PREPARATION XLI

N-[(2,4-Dimethyl-3-(chlorocarbonyl)phenyl) sulfonyl]-L-proline methyl ester

A suspension of 0.77 g (2.26.10$^{-3}$ mol) of the acid obtained according to Preparation XL in 25 ml of toluene is prepared and 0.30 g (2.5.10$^{-3}$ mol) of thionyl chloride is added. The reaction mixture is refluxed for 4 hours, with stirring, and then concentrated under reduced pressure. The oily residue crystallizes on cooling to give 0.80 g of the expected product in the form of a beige solid (yield=98%).

M.p.=92° C.

$[\alpha]_D^{26}$=−13° (c=0.33; CHCl$_3$)

PREPARATION XLII

N-[(2,4-Dimethyl-3-(hydroxymethyl)phenyl) sulfonyl]-L-proline methyl ester

A solution of 0.83 g (2.31.10$^{-3}$ mol) of the acid chloride obtained according to Preparation XLI in 30 ml of diglyme is prepared and 0.1 g of sodium borohydride is added in portions at 80° C. The reaction mixture is stirred for 30 minutes at 80° C. and then cooled. Water is added and the mixture is extracted 3 times with ethyl acetate. The combined organic phases are washed with water, dried over magnesium sulfate and then concentrated under reduced pressure. The crude product is purified by chromatography on silica gel using a dichloromethane/ethyl acetate mixture (9/1; v/v) as the eluent to give 500 mg of the expected product in the form of an oil (yield=69%).

$[\alpha]_D^{26}$=−28.5° (c=0.66; CH$_3$OH)

PREPARATION XLIII

N-1-[[2,4-Dimethyl-3-(methylsulfonylmethyl) phenyl]sulfonyl]-L-proline methyl ester A solution of 0.46 g (1.4.10$^{-3}$ mol) of the alcohol obtained according to Preparation XLII in 7 ml of dichloromethane is cooled to 0° C. and 0.356 g (3.5.10$^{-3}$ mol) of triethylamine and then 0.37 g (3.2.10$^{-3}$ mol) of methanesulfonyl chloride are added. The mixture is stirred for 3 hours at room temperature and subsequently washed with sodium bicarbonate solution and then with water. The organic phase is dried and then concentrated under reduced pressure to give 0.57 g of an oil containing predominantly the expected product and the corresponding chloromethylated derivative. This oil is used directly for the next step.

PREPARATION XLIV

N-[[3-[(2,4-Dimethylquinolin-8-yl)oxymethyl]-2,4-dimethylphenyl]sulfonyl]-L-proline methyl ester 45 mg ($1.5.10^{-3}$ mol) of sodium hydride (as an 80% suspension in oil) are added to a solution of 0.23 g ($1.3.10^{-3}$ mol) of 2,4-dimethyl-8-hydroxyquinoline in 5 ml of dimethylformamide. After stirring for 30 minutes at room temperature, a solution of 550 mg of the compound obtained according to Preparation XLIII in 3 ml of dimethylformamide is added. After stirring for 3 hours at room temperature, the reaction mixture is poured into 100 ml of iced water and extracted twice with ethyl acetate. The combined organic phases are washed with water, dried over magnesium sulfate and concentrated under reduced pressure. The residue is purified by chromatography on silica gel using a dichloromethane/ethyl acetate mixture (80/20; v/v) as the eluent to give 367 mg of the expected product in the form of an amorphous solid (yield=56%).

M.p.=50° C.

$[\alpha]_D^{26}$=-15° (c=0.39; $CH_3OH$)

PREPARATION XLV

N-[[3-[(2,4-Dimethylquinolin-8-yl)oxymethyl]-2,4-dimethylphenyl]sulfonyl]-L-proline The expected product is obtained in the form of a white solid (yield=88%) by following a procedure analogous to Preparation XXXIII, starting from the compound obtained according to Preparation XLIV.

M.p.=136° C.

$[\alpha]_D^{26}$=-67° (c=0.57; $CH_3OH$)

PREPARATION XLVI

1-[[3-[(2,4-Dimethylquinolin-8-yl)oxymethyl]-2,4-dimethylphenyl]sulfonyl]-N-[3-[(4-cyanophenyl)carbonylamino]propyl]-2(S)-pyrrolidinecarboxamide The expected product is obtained in the form of white crystals (yield=78%) by following a procedure analogous to Preparation V, starting from the compounds obtained according to Preparations XLV and XXXV.

M.p.=68° C.

$[\alpha]_D^{23}$=-28° (c 0.33; $CH_3OH$)

PREPARATION XLVII

1-[[3-[(2,4-Dimethylquinolin-8-yl)oxymethyl]-2,4-dimethylphenyl]sulfonyl]-N-[3-[[4-[(amino)(hydroxyimino)methyl]phenyl]carbonylamino]propyl]-2(S)-pyrrolidinecarboxamide The expected product is obtained in the form of a white solid (yield=93%) by following a procedure analogous to Preparation II, starting from the compound obtained according to Preparation XLVI.

M.p.=130° C.

$[\alpha]_D^{23}$=-23° (c 0.40; $CH_3OH$)

PREPARATION XLVIII

1-[[3-[(2,4-Dimethylquinolin-8-yl)oxymethyl]-2,4-dimethylphenyl]sulfonyl]-N-[3-[[4-[(amino)(acetoxyimino)methyl]phenyl]carbonylamino]propyl]-2(S)-pyrrolidinecarboxamide The expected product is obtained in the form of white crystals (yield=93%) by following a procedure analogous to Preparation III, starting from the compound obtained according to Preparation XLVII.

M.p.=60° C.

$[\alpha]_D^{23}$=-24° (c=0.39; $CH_3OH$)

EXAMPLE 34

1-[[3-[(2,4-Dimethylquinolin-8-yl)oxymethyl]-2,4-dimethylphenyl]sulfonyl]-N-[3-[[4(aminoiminomethyl)phenyl]carbonylamino]propyl]-2(S)-pyrrolidinecarboxamide The expected product is obtained in the form of a white solid (yield=79%) by following a procedure analogous to Example 11, starting from the compound obtained according to Preparation XLVIII.

M.p.=150° C.

$[\alpha]_D^{23}$=-35° (c=0.39; $CH_3OH$)

EXAMPLE 35

1-[[3-[(2,4-Dimethylquinolin-8-yl)oxymethyl]-2,4-dimethylphenyl]sulfonyl]-N-[3-[[4(aminoiminomethyl)phenyl]carbonylamino]propyl]-2(S)-pyrrolidinecarboxamide dihydrochloride A solution of 0.56 g ($0.83.10^{-3}$ mol) of the compound obtained according to Example 34 in 4 ml of methanol is prepared and 1 ml of a saturated solution of hydrogen chloride in ethyl ether is added. After the mixture has been stirred for 15 min, 50 ml of ethyl ether are added. The precipitate formed is filtered off, washed with ether, dried in a desiccator and then dissolved in 10 ml of water. The solution obtained is filtered and lyophilized to give 0.58 g of the expected product in the form of a white powder (yield=94%).

M.p.=195° C.

$[\alpha]_D^{19}$=-86° (c 0.47; $CH_3OH$)

EXAMPLE 36

1-[[3-[(2,4-Dimethylquinolin-8-yl)oxymethyl]-2,4-dichlorophenyl]sulfonyl]-N-[3-[[4-(aminoiminomethyl)phenyl]carbonylamino]propyl]-2(S)-pyrrolidinecarboxamide di(methanesulfonate)

A solution of 1.59 g ($16.5.10^{-3}$ mol) of methanesulfonic acid in 15 ml of methanol is prepared and a methanol solution of 5.87 g ($8.25.10^{-3}$ mol) of the compound obtained according to Example 5 is added slowly, with stirring. The mixture is stirred for 30 minutes at room temperature and the solution obtained is then poured into 600 ml of ethyl ether. The white precipitate formed is filtered off, washed with ether on the filter and then dried in a desiccator under vacuum and redissolved in 50 ml of water. The solution obtained is filtered and then lyophilized to give 6.6 g of the expected product in the form of a white powder (yield=88%).

M.p.=174–176° C.

$[\alpha]_D^{24}$=-29° (c=0.30; $CH_3OH$)

The activity of the products according to the invention was evaluated in respect of their ability to bind to the bradykinin receptors. Kinins, of which bradykinin is the main representative, actually form a group of small peptides which make an important contribution to the inflammatory response and therefore appear to be involved in the pathophysiology of inflammatory diseases. Furthermore, bradykinin is one of the most potent analgesics known. Kinins activate two types of receptor, called $B_1$ and $B_2$. The $B_2$ receptor belongs to the large family of receptors with seven transmembrane domains coupled to the G proteins. In the present invention we describe compounds which bind to the $B_2$ receptor and thereby block the binding of bradykinin.

The following pharmacological test is used: Ileum segments are isolated from male guinea-pigs [of the Dunkin-Hartley strain (Iffa Credo, l'Arbresle, France)] and ground in the following TES buffer: TES 25 mM, 1,10-phenanthroline 1 mM (pH 6.8), bacitracin 140 μg/ml, BSA 1 g/l. The membranes are then isolated by centrifugation (18,000 rpm; 20 min; 4° C.). The binding studies are carried out in this TES buffer using [$^3$H]-bradykinin (120 pM) and 50 μg of membrane protein per test (final volume 500 μl) with an equilibrium time of 90 min at 20° C. The percentage inhibition of the binding of [$^3$H]-bradykinin is then determined in the presence of one of the test compounds according to the invention at a concentration of $10^{-6}$ M.

The results obtained from these tests (shown as "activity") are collated in Table I below with reference to the Examples given in the description. In this Table, Pos indicates the position of the amidine group on the aromatic (or heteroaromatic) ring relative to the group B; in the "Salt" column, Chl denotes that the compound is in the form of the hydrochloric acid salt and Ms denotes that it is in the form of the methanesulfonic acid salt.

The compounds of the present invention which inhibit the binding of [3H]-bradykinin to the guinea-pig $B_2$ receptor (see Table I) also bind to the human $B_2$ receptor cloned and transfected in a stable manner into CHO cells (Chinese Hamster Ovary cells). Thus, in this test, some compounds inhibit the binding of [$^3$H]-bradykinin to the $B_2$ receptor by at least 95% at a concentration of 10 μM.

The compounds of the present invention can be useful in the treatment of pain and particularly in the treatment of numerous pathological conditions involving bradykinin or its homologs. These pathological conditions include septic and hemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angioedema, migraine, encephalomyelitis, meningitis, cerebrovascular complications (especially those caused by cerebral traumatic shock), certain neurological disorders, vascular inflammatory states (for example atherosclerosis and arteritis of the lower limbs), painful states (for example headache, toothache, menstrual pain), premature uterine contractions, cystitis and burns. The compounds according to the invention can also be useful for the potentiation of antiviral agents.

The compounds of the present invention, which can be used in the form of the free base or in the form of their non-toxic addition salts in association with a physiologically acceptable excipient, are generally prescribed in human therapeutics at doses of about 1 to 1000 mg/day in a form which can be administered orally, by intravenous, intramuscular or subcutaneous injection, transdermally, by means of aerosols or by means of suppositories.

These compounds can also be administered topically, for example in the form of a gel or ointment.

The compounds of the present invention are also useful as pharmacological reagents, especially for the study of hormone-receptor interactions. Use as a pharmacological reagent may require a radiolabeled derivative of one of the compounds according to the invention (for example with tritium [3H] or sulfur [$^{35}$S]) in order to obtain a radioligand intended for conformational studies of the bradykinin $B_2$ receptor or for binding tests involving this type of receptor, for example for the evaluation of novel compounds which are capable of exhibiting an affinity for the bradykinin $B_2$ receptor.

TABLE I

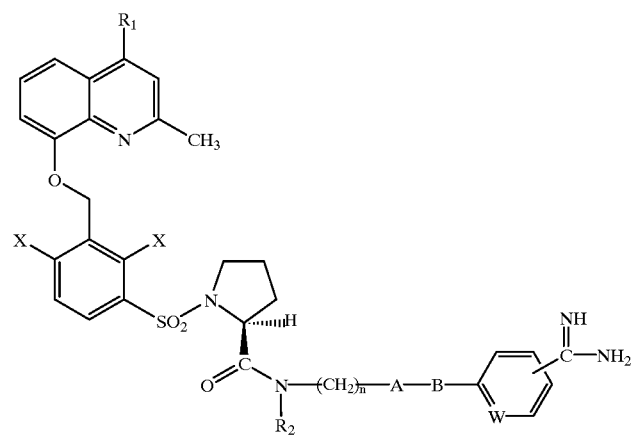

(I)

| Ex | X | A | B | $R_1$ | $R_2$ | n | W | Pos | Salt | Activity |
|---|---|---|---|---|---|---|---|---|---|---|
| 1 | Cl | —NH—CO— | — | $CH_3$ | H | 2 | CH | 4 | — | — |
| 2 | Cl | —NH—CO— | — | $CH_3$ | H | 2 | CH | 4 | Chl | 92 |
| 3 | Cl | —NH—CO— | —$CH_2$—O— | $CH_3$ | H | 2 | CH | 4 | — | — |
| 4 | Cl | —NH—CO— | —$CH_2$—O— | $CH_3$ | H | 2 | CH | 4 | Chl | 95.5 |
| 5 | Cl | —NH—CO— | — | $CH_3$ | H | 3 | CH | 4 | — | — |
| 6 | Cl | —NH—CO— | — | $CH_3$ | H | 3 | CH | 4 | Chl | 99 |

TABLE I-continued

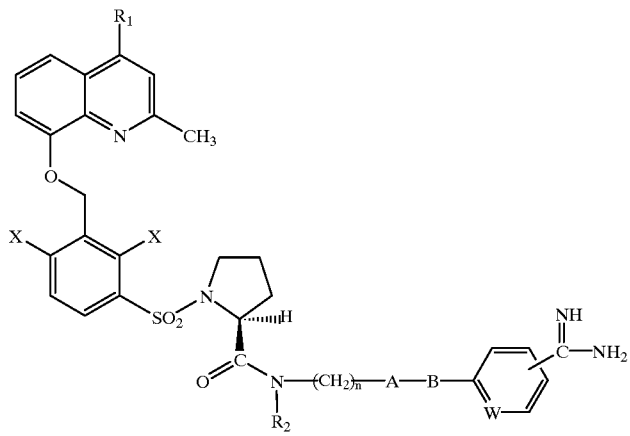

| Ex | X | A | B | R₁ | R₂ | n | W | Pos | Salt | Activity |
|---|---|---|---|---|---|---|---|---|---|---|
| 7 | Cl | —NH—CO— | —CH₂— | CH₃ | H | 3 | CH | 4 | — | — |
| 8 | Cl | —NH—CO— | —CH₂— | CH₃ | H | 3 | CH | 4 | Chl | 97.5 |
| 9 | Cl | —NH—CO— | —CH₂—O— | CH₃ | H | 3 | CH | 4 | — | — |
| 10 | Cl | —NH—CO— | —CH₂—O— | CH₃ | H | 3 | CH | 4 | Chl | 98.8 |
| 11 | Cl | —NH—CO— | — | CH₃ | H | 3 | CH | 3 | — | — |
| 12 | Cl | —NH—CO— | — | CH₃ | H | 3 | CH | 3 | Chl | — |
| 13 | Cl | —N(Et)—CO— | — | CH₃ | H | 3 | CH | 4 | — | — |
| 14 | Cl | —N(Et)—CO— | — | CH₃ | H | 3 | CH | 4 | Chl | 97 |
| 15 | Cl | —N(Me)—CO— | — | CH₃ | H | 3 | CH | 4 | — | — |
| 16 | Cl | —N(Me)—CO— | — | CH₃ | H | 3 | CH | 4 | Chl | 100 |
| 17 | Cl | —NH—CO— | — | H | H | 3 | CH | 4 | — | — |
| 18 | Cl | —NH—CO— | — | H | H | 3 | CH | 4 | Chl | — |
| 19 | Cl | —NH—CO— | — | CH₃ | H | 4 | CH | 4 | Chl | 98 |
| 20 | Cl | —NH—CO— | — | CH₃ | H | 5 | CH | 4 | — | — |
| 21 | Cl | —NH—CO— | — | CH₃ | CH₃ | 5 | CH | 4 | Chl | 100 |
| 22 | Cl | —NH—CO— | — | CH₃ | CH₃ | 3 | CH | 4 | — | — |
| 23 | Cl | —NH—CO— | — | CH₃ | CH₃ | 3 | CH | 4 | Chl | — |
| 24 | Cl | —N(Me)—CO— | — | CH₃ | CH₃ | 3 | CH | 4 | — | — |
| 25 | Cl | —N(Me)—CO— | — | CH₃ | CH₃ | 3 | CH | 4 | Chl | — |
| 26 | Cl | —NH—CO— | — | CH₃ | H | 3 | N | 4 | — | — |
| 27 | Cl | —NH—CO— | — | CH₃ | H | 3 | N | 4 | Ms | — |
| 28 | Cl | —CO—NH— | —CH₂— | CH₃ | H | 3 | CH | 4 | | — |
| 29 | Cl | —CO—NH— | —CH₂— | CH₃ | H | 3 | CH | 4 | Chl | — |
| 30 | Cl | —CO—NH— | — | CH₃ | H | 3 | CH | 4 | | — |
| 31 | Cl | —CO—NH— | — | CH₃ | H | 3 | CH | 4 | Chl | — |
| 32 | Cl | —NH—CO— | — | CF₃ | H | 3 | CH | 4 | — | — |
| 33 | Cl | —NH—CO— | — | CF₃ | H | 3 | CH | 4 | Ms | — |
| 34 | CH₃ | —NH—CO— | — | CH₃ | H | 3 | CH | 4 | — | — |
| 35 | CH₃ | —NH—CO— | — | CH₃ | H | 3 | CH | 4 | Chl | — |
| 36 | Cl | —NH—CO— | — | CH₃ | H | 3 | CH | 4 | Ms | — |

Notes
Chl: hydrochloric acid salt
Ms: methanesulfonic acid salt
Pos: position of the amidine group relative to B [the amidine group of Ex. 26 and Ex. 27 is in the 5-position on the pyridinyl ring (W = N)]

What is claimed is:

1. An N-(benzenesulfonyl)-L-proline compound selected from the group consisting of:

(i) formula I:

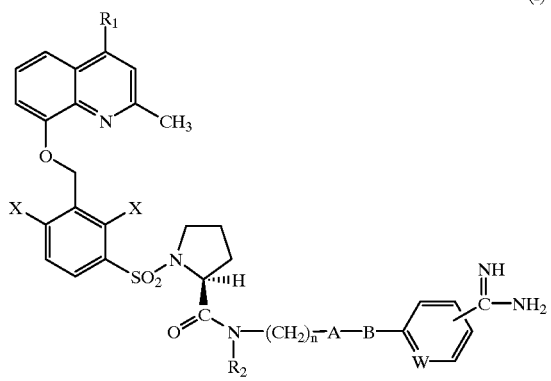

in which:

X is a halogen atom or a methyl group,
A is a group —N(R$_3$)—CO— or —CO—N(R$_3$)—,
B is a single bond, —CH$_2$— or —CH$_2$—O—,
R$_1$ is a hydrogen atom a C$_1$–C$_3$ alkyl group or a trifluoromethyl group,
R$_2$ and R$_3$ are each independently a hydrogen atom or a C$_1$–C$_3$ alkyl group,
W is CH or N, and
n is 2, 3, 4 or 5; and (ii) their addition salts.

2. A compound according to claim 1 wherein X is Cl.

3. A process for the preparation of a compound of formula I, said process comprising:

(1) reacting an acid of formula II:

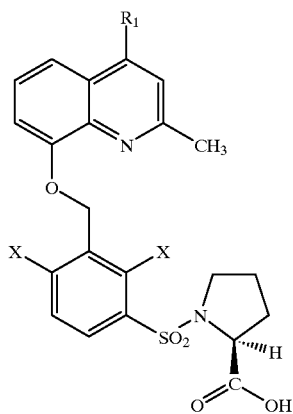

in which:

R$_1$ is a hydrogen atom, a C$_1$–C$_3$ alkyl group or a trifluoromethyl group, and
X is a halogen or a methyl group, with an amine of formula III:

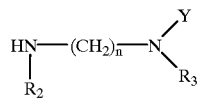

in which:

R$_2$ and R$_3$ are each independently H or a C$_1$–C$_3$ alkyl group,
n is 2, 3, 4 or 5, and
Y is an amino-protecting group, in a solvent, in the presence of at least one activator commonly used to create linkages of the peptide type, at a temperature between about 0 and about 40° C., for 2 to 50 hours, to give a compound of formula IV:

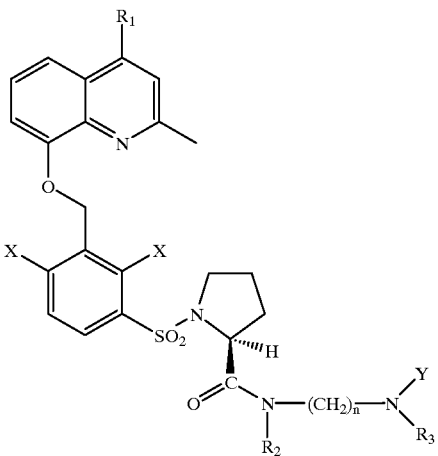

in which R$_1$, R$_2$, R$_3$, X, Y and n are as defined above;

(2) deprotecting the resulting compound of formula IV to replace the protecting group Y with a hydrogen atom, in a solvent, at a temperature of 0–40° C., for 5 to 30 hours, to give the compound of formula V:

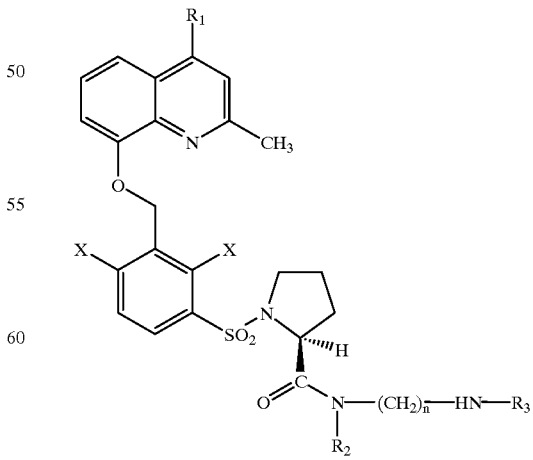

in which R$_1$, R$_2$, R$_3$, X and n are as defined above;

(3) reacting the resulting compound of formula V with an acid of formula VI:

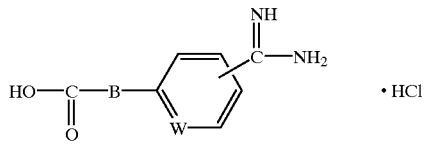

(VI) · HCl in which:
B is a single bond or a group —CH$_2$— or —CH$_2$—O—, and
W is —CH— or a nitrogen atom,
under conditions analogous to those recommended for step (1), and, if necessary, in the presence of a base if the amine of formula V is reacted in its salified form, to give the compound of formula I:

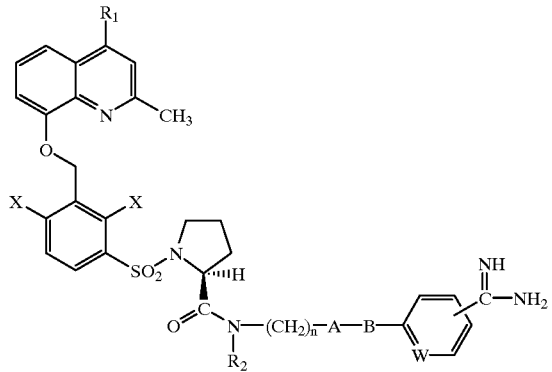

(I)

in which:
A is —N(R$_3$)—CO—,
B is a single bond, —CH$_2$— or —CH$_2$—O—,
R$_1$ is H, a C$_1$–C$_3$ alkyl group or a trifluoromethyl group,
R$_2$ and R$_3$ are each independently H or a C$_1$–C$_3$ alkyl group,
X is a halogen atom or a methyl group,
W is CH or N, and
n is 2, 3, 4 or 5; and (4) if necessary, reacting the resulting compound of formula I, in the form of the base, with a mineral or organic acid to give said compound of formula I in the form of an addition salt.

4. A process for the preparation of a compound of formula I according to claim 3, said process comprising:

(a) reacting the compound of formula V, obtained in step (2), with a compound of formula VIII:

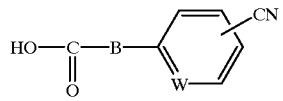

(VIII)

in which:
B is a single bond, —CH$_2$— or —CH$_2$O—, and
W is CH or N,
under operating conditions analogous to those of step (3), to give a compound of formula IX:

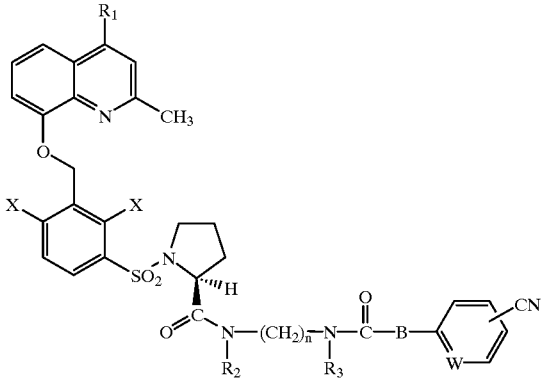

(IX)

in which R$_1$, R$_2$, R$_3$, X, W, n and B are as defined in the starting materials;

(b) reacting the resulting compound of formula IX with hydroxylamine, in a solvent, at a temperature of 0–40° C., for 2 to 12 hours, to give the compound of formula X:

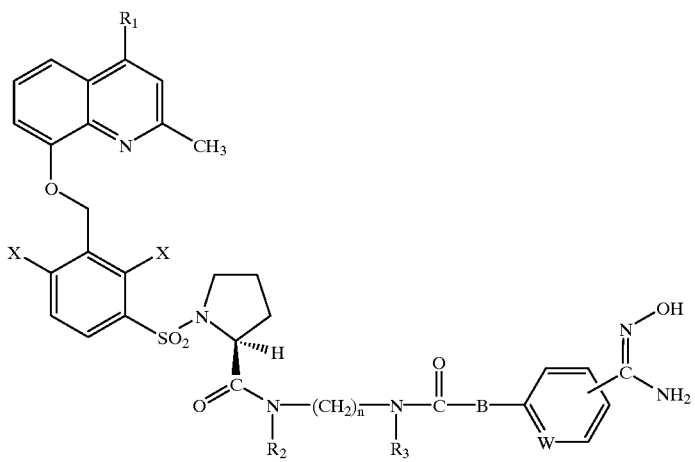

(X)

in which $R_1$, $R_2$, $R_3$, X, W, n and B are as defined above;

(c) reacting the resulting compound of formula X with excess acetic anhydride in a solvent, at a temperature of 0–40° C., for 1 to 15 hours, to give the compound of formula XI:

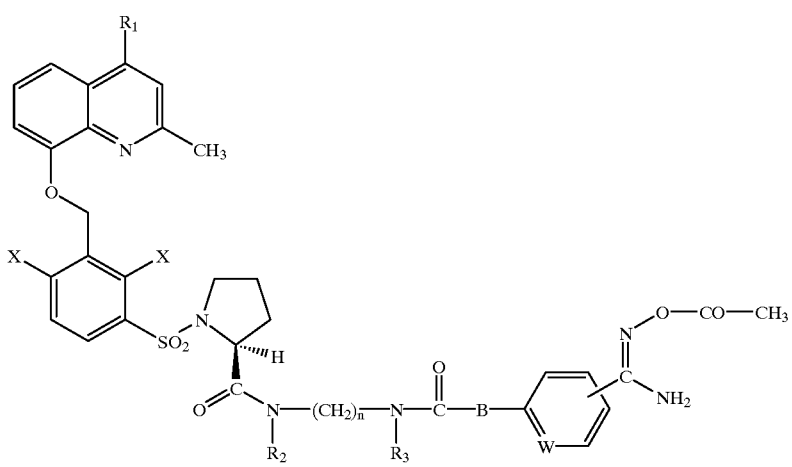

(XI)

in which $R_1$, $R_2$, $R_3$, X, W, n and B are as defined above;

(d) catalytically hydrogenating the resulting compound of formula XI in a solvent, in the presence of a hydrogenation catalyst, at a temperature of 0–40° C., under a hydrogen pressure of between $10^5$ and $5.10^5$ Pa, to give the compound of formula I in which $R_1$, $R_2$, $R_3$, X, W, n and B are as defined above, A is the group —$N(R_3)$—CO— and the amidine group retains the initial position of the cyano group of the starting acid; and (e) if necessary, reacting the resulting compound of formula I, in the form of the base, with a mineral or organic acid to give said compound of formula I in the form of an addition salt.

5. A process according to claim 3 wherein, in step (3), (i) the acid of formula VI is replaced with the corresponding acid chloride, and (ii) the reaction is carried out in a solvent in the presence of an aprotic base.

6. A therapeutic composition containing, in association with a physiologically acceptable excipient, at least one compound selected from the group consisting of a compound of formula I and their non-toxic acid addition salts according to claim 1.

7. A method of treating a pathological condition involving bradykinin or its homolog comprising administering an effective amount of a bradykinin $B_2$ receptor antagonist selected from the group consisting of the compounds of formula I and their non-toxic addition salts according to claim 1.

8. A method according to claim 7 wherein said pathological condition involving bradykinin or its homologs is pain.

9. A method according to claim 7 wherein said pathological condition involving bradykinin or its homologs is inflammation.

10. A method of studying hormone-bradykinin interactions comprising binding a compound of formula I or one of its acid addition salts according to claim 1 to a bradykinin $B_2$ receptor.

11. The process of claim 3, wherein in the reaction of step (1) is carried out at a temperature of between 10 and 35° C.

12. The process of claim 3, wherein in the reaction of step (2) is carried out at a temperature of between 15 and 25°C.

* * * * *